United States Patent
Hirohara et al.

(10) Patent No.: US 6,525,883 B2
(45) Date of Patent: Feb. 25, 2003

(54) OPTICAL CHARACTERISTIC MEASURING INSTRUMENT

(75) Inventors: Yoko Hirohara, Tokyo (JP); Naoki Nakazawa, Tokyo (JP); Toshifumi Mihashi, Tokyo (JP)

(73) Assignee: Kabushiki Kaisha Topcon (JP)

( * ) Notice: Subject to any disclaimer, the term of this patent is extended or adjusted under 35 U.S.C. 154(b) by 0 days.

(21) Appl. No.: 09/914,439
(22) PCT Filed: Dec. 27, 2000
(86) PCT No.: PCT/JP00/09288

§ 371 (c)(1),
(2), (4) Date: Mar. 20, 2002

(87) PCT Pub. No.: WO01/47407

PCT Pub. Date: May 7, 2001

(65) Prior Publication Data

US 2003/0011757 A1 Jan. 16, 2003

(30) Foreign Application Priority Data

Dec. 27, 1999 (JP) ............................................. 11-371951
Dec. 8, 2000 (JP) ....................................... 2000-375206

(51) Int. Cl.⁷ ............................. G02B 27/10; A61B 3/10
(52) U.S. Cl. ........................................ 359/618; 351/212
(58) Field of Search ......................... 359/618; 356/124; 351/212, 221

(56) References Cited

U.S. PATENT DOCUMENTS

2001/0035939 A1 * 11/2001 Mihashi et al. .............. 351/212
2002/0005940 A1 * 1/2002 Hatada et al. ................ 355/55
2002/0041359 A1 * 4/2002 Mihashi et al. .............. 351/221

* cited by examiner

Primary Examiner—Georgia Epps
Assistant Examiner—Omar Hindi
(74) Attorney, Agent, or Firm—Baker Botts LLP

(57) ABSTRACT

The present invention relates to an apparatus for precise measurement of optical characteristics, and has an object to provide an optical characteristic measuring apparatus comprising a position change unit for changing the positions of beams transformed by a first transforming member, wherein a first light source emits a luminous flux of a first wavelength, a first illumination optical system illuminates a minute area on the retina of the eye under examination with the luminous flux from the first light source, a first light receiving optical system leads light to a first light receiving unit through a transforming member for transforming the luminous flux having undergone at least one of transmission and reflection at at least one surface of the object of measurement into at least nine beams, a position change unit changes the positions of the beams transformed by the first transforming member, and an arithmetic unit can determine optical characteristics of the object of measurement based on a first signal from the first light receiving unit corresponding to the angle of inclination of the luminous flux.

12 Claims, 26 Drawing Sheets

(b)

(a)

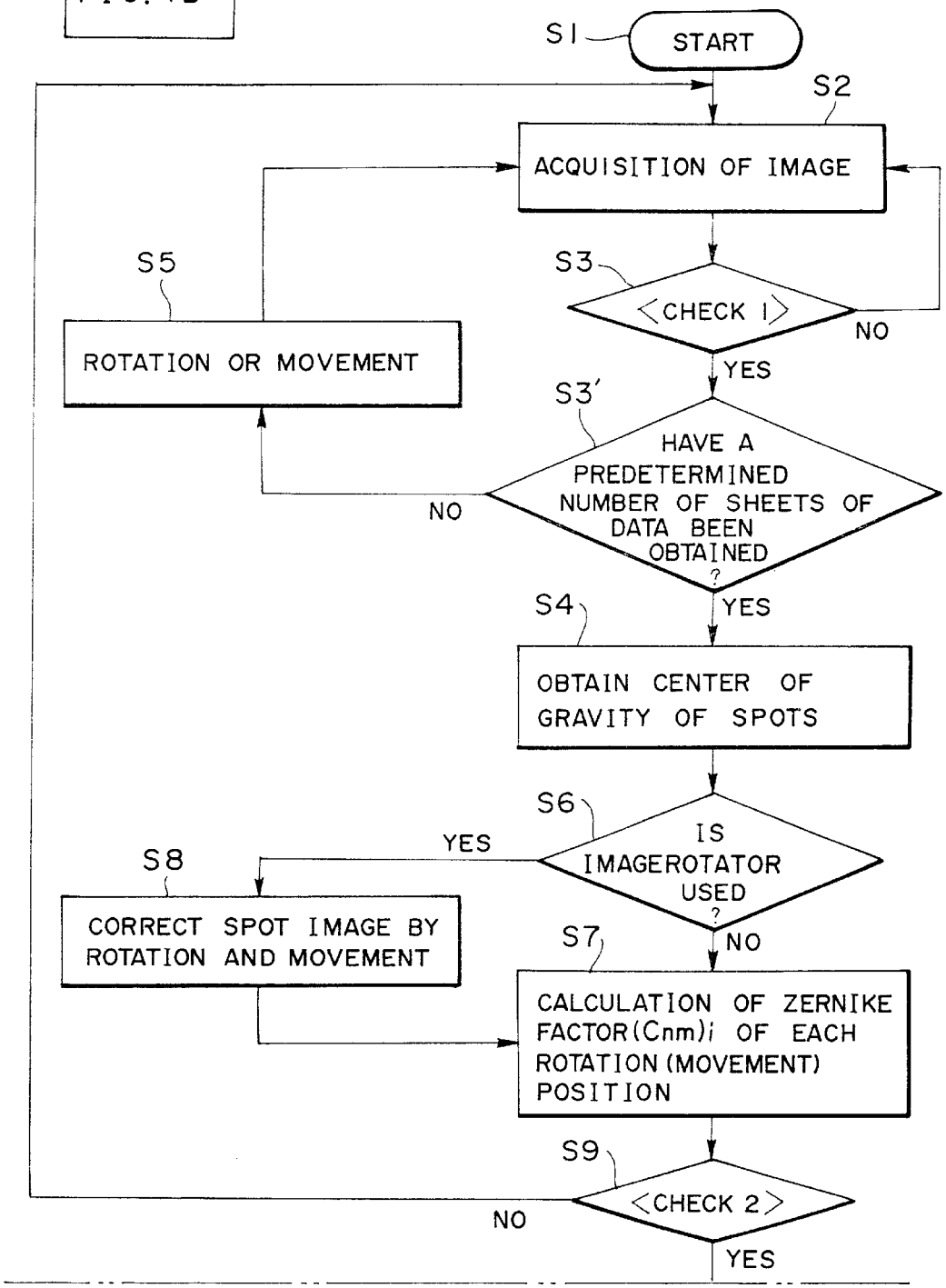

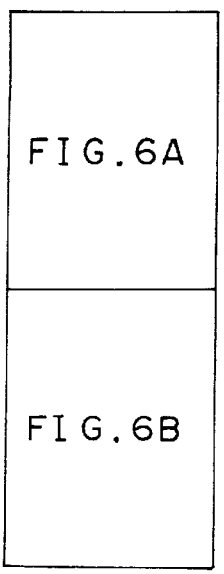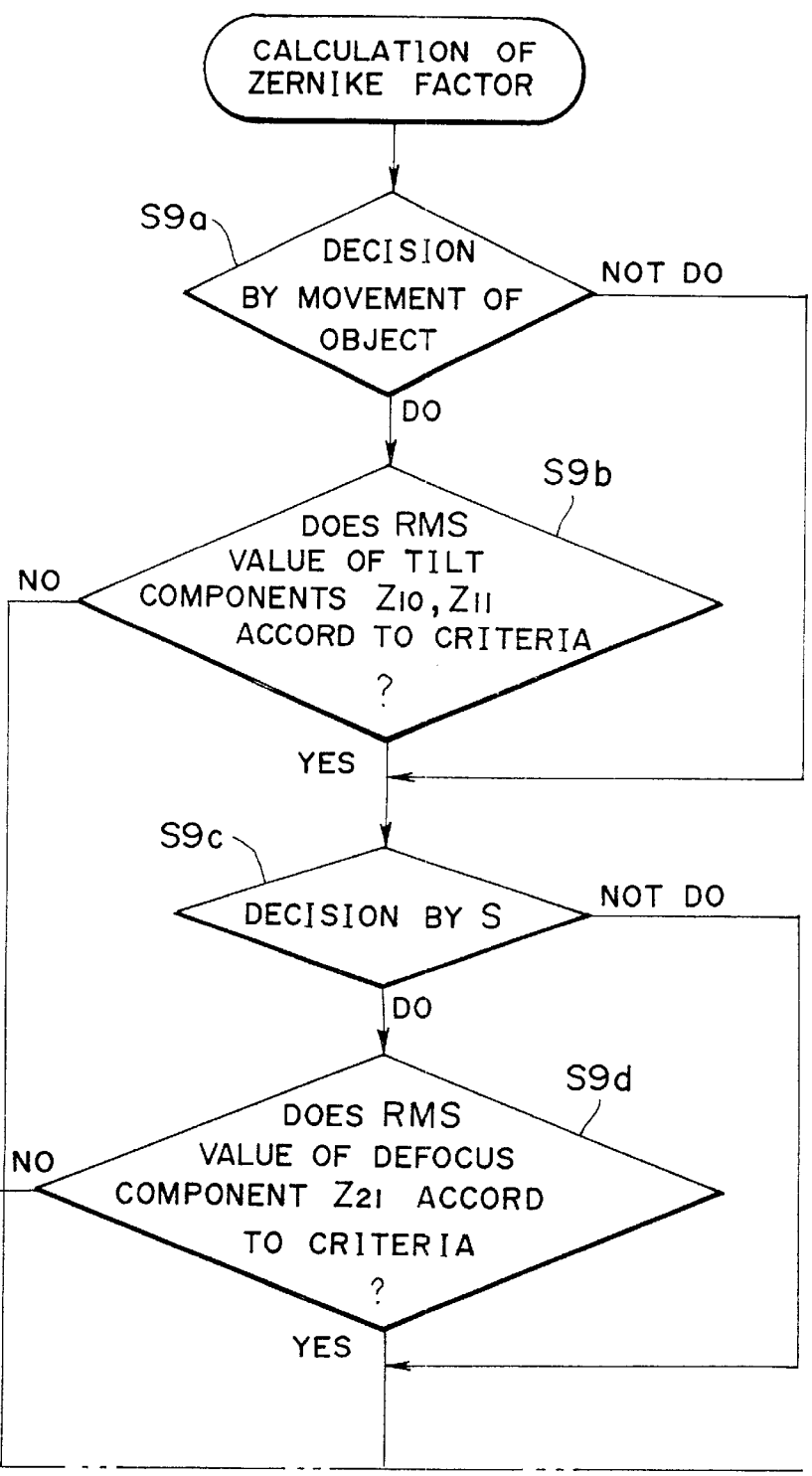

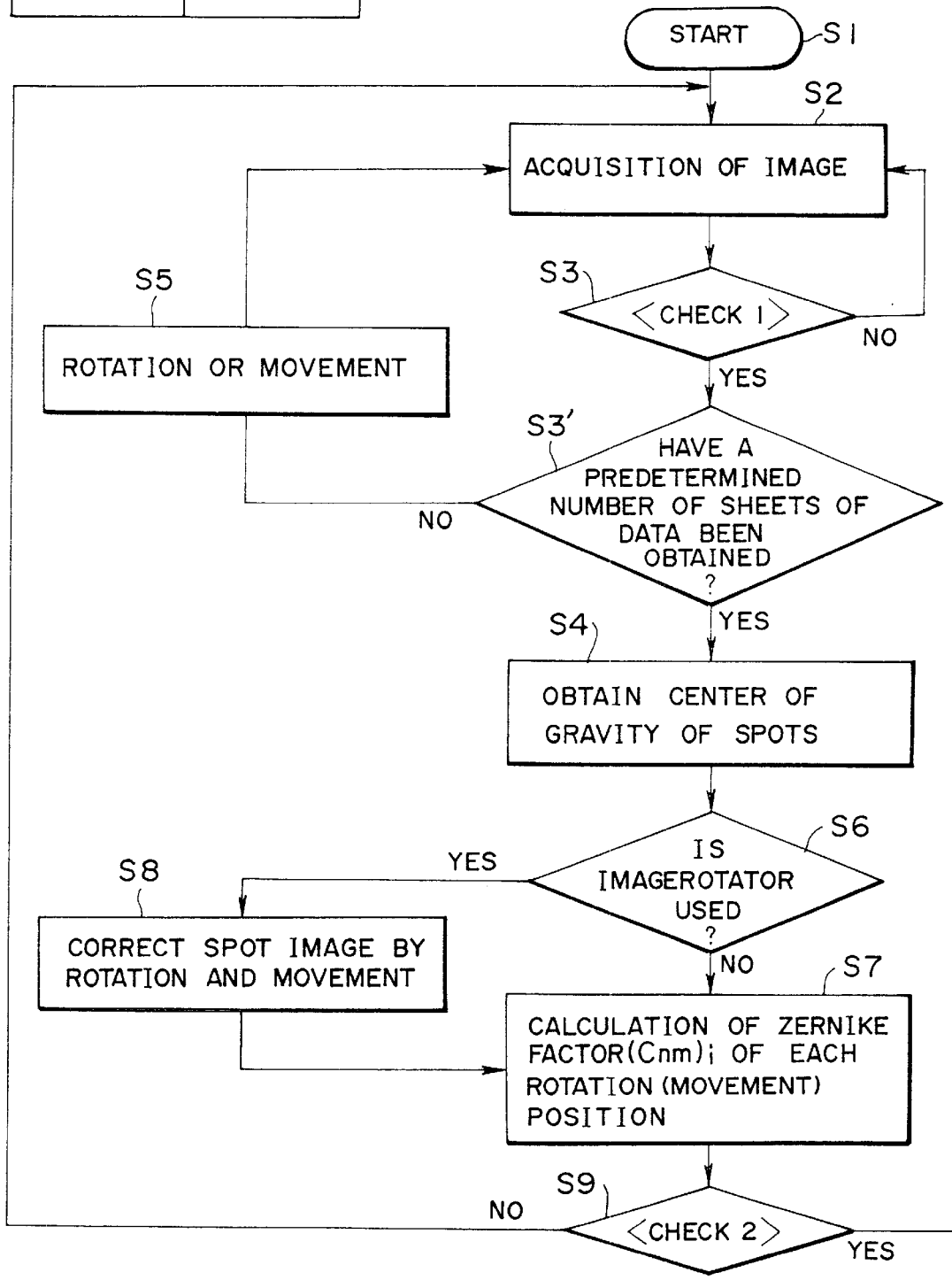

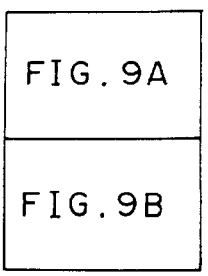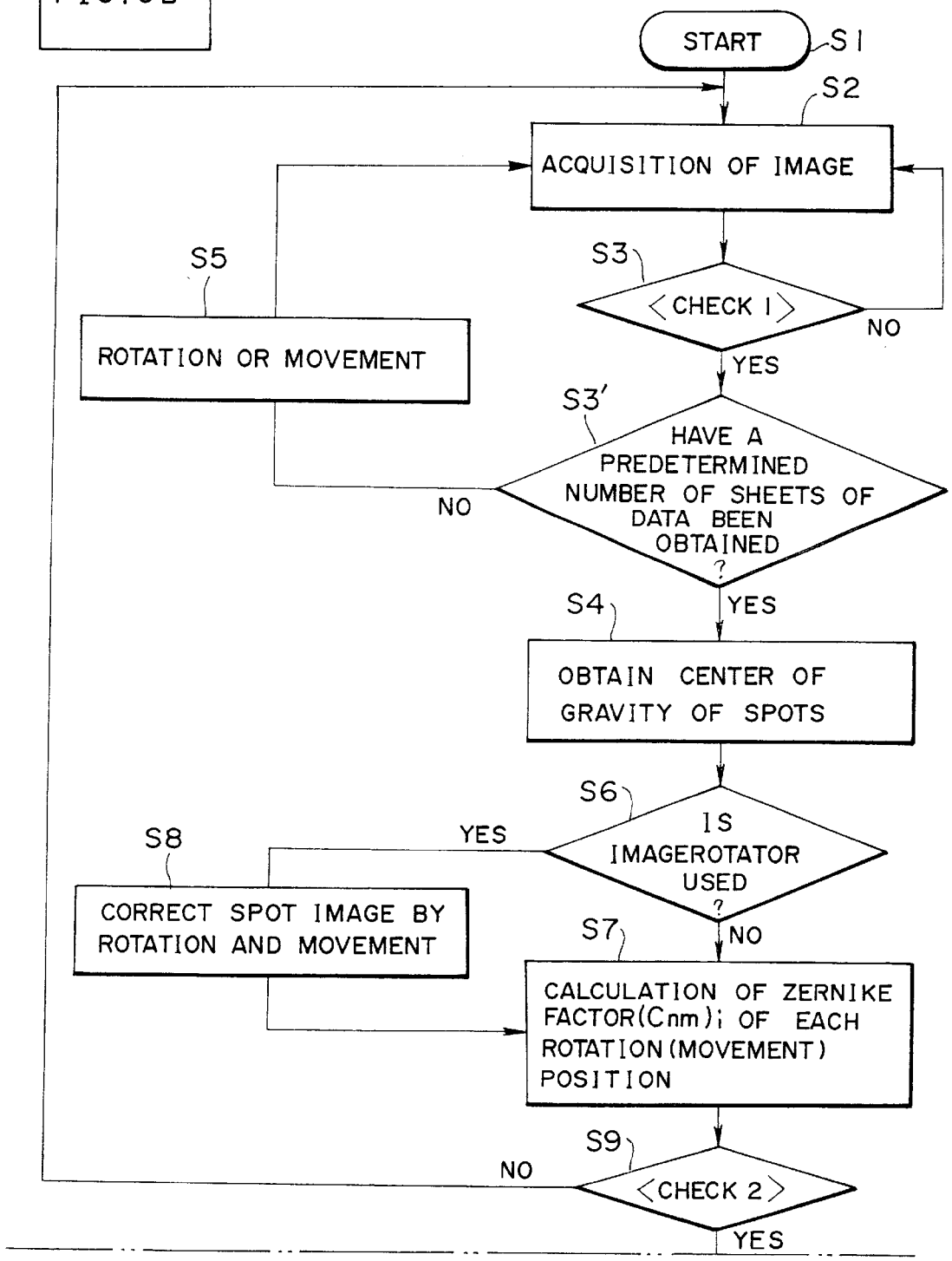

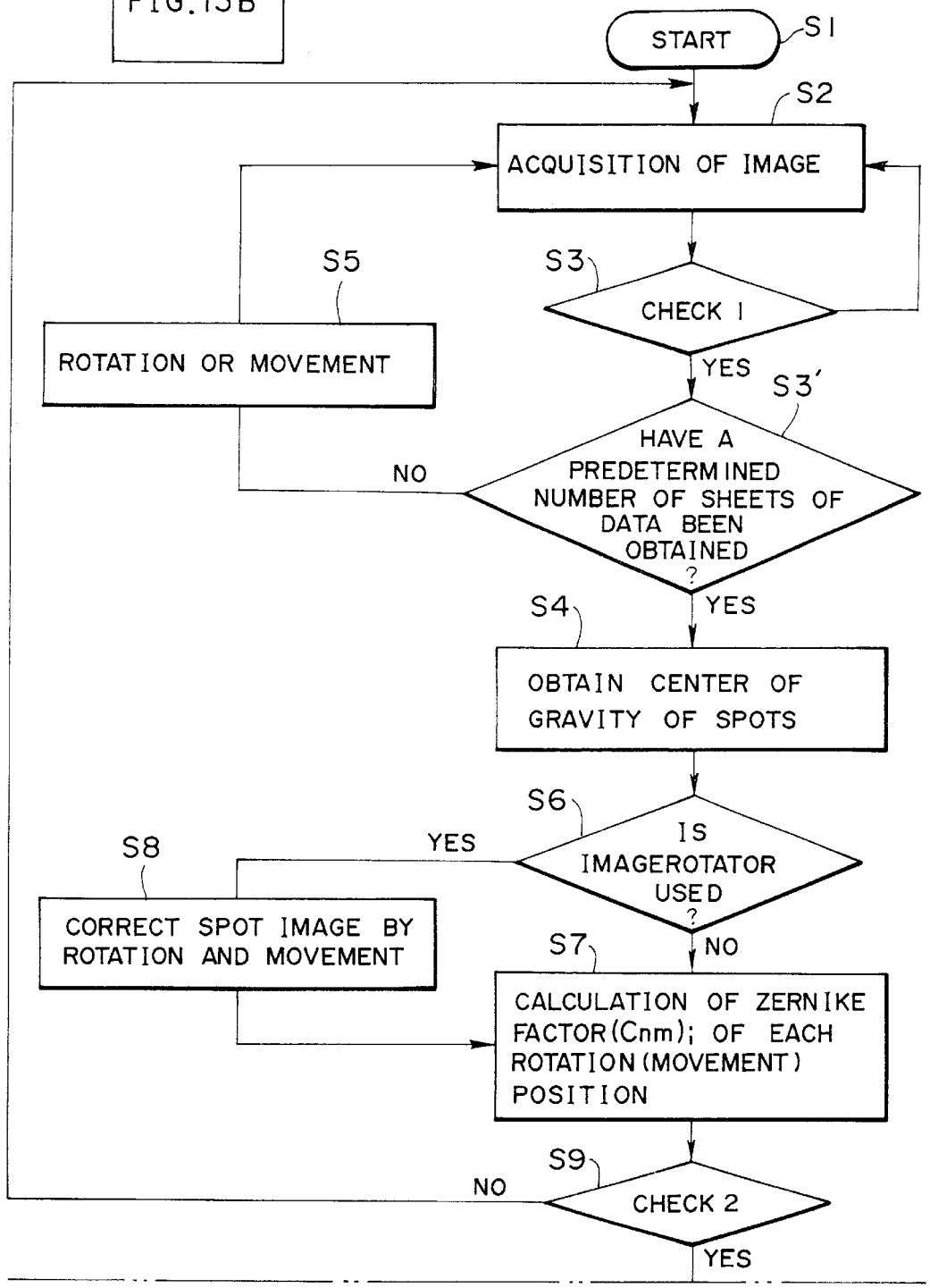

OPTICAL CHARACTERISTIC MEASURING INSTRUMENT

This application is a 371 of PCT/JP00/09288, Dec. 27, 2000.

TECHNICAL FIELD

The present invention relates to an apparatus for precise measurement of optical characteristics, and particularly to an optical characteristic measuring apparatus comprising a position change unit for changing the positions of beams transformed by a first transforming member.

BACKGROUND ART

Among optical characteristic measuring apparatuses, there has been an apparatus disclosed in a patent application made by the present applicant, in which the focus in an illumination optical system is adjusted based on a light reception level of a first light receiving unit and the focus of a light receiving optical system is adjusted based on an optical characteristic (S) determined from an output of the first light receiving unit (Japanese Patent Application No. 9-137630 (1997)).

In addition, the present applicant has applied an apparatus for measuring optical characteristics by use of a plurality of beams by a beam transforming member known as a Hartmann plate (Japanese Patent Application No. 9-42940 (1997)).

However, in order to measure with high precision, it is necessary to use a transforming member with a high density of openings. In a transforming member with a high density of openings, the quantity of light for one opening is small. Besides, there is the drawback that when one opening is reduced, the size of the lens comes to be on the same order as a diffraction limit image. As a result, there is the problem that, depending on the positional relationship between adjacent spots, it is impossible to specify the spots.

DISCLOSURE OF INVENTION

The present invention may resides in that a first light source emits a luminous flux of a first wavelength, a first illumination optical system illuminates a minute area on the retina of an eye under examination by the luminous flux from the first light source, a first light receiving optical system leads light to a first light receiving unit through a transforming member for transforming the luminous flux having undergone at least one of transmission and reflection at at least one surface of the object of measurement into at least nine beams, a position change unit changes the positions of the beams transformed by the first transforming member, and an arithmetic unit can determine optical characteristics of the object of measurement based on a first signal from the first light receiving unit corresponding to the angle of inclination of the luminous flux.

In addition, the position change unit according to the invention may change the positions of the beams transformed by the first transforming member by at least one of linear movement and rotational movement of the first transforming member.

Besides, the position change unit according to the invention may move the first transforming member to at least one of mechanical constitution and optical constitution.

Further, the position change unit according to the invention may change the positions of the beams transformed by the first transforming member by at least one of linear movement and rotational movement of the first transforming member, whereby the transformed beam positions after the change are located at roughly middle positions of the transformed beams before the change.

In addition, the arithmetic unit according to the invention may calculate optical characteristics of the object of measurement based on data before and after the change of beam positions, and may determine a process according to the deviations of the optical characteristics.

Further, the arithmetic unit according to the invention may prompt re-measurement based on the data before and after the change of beam positions when the optical characteristics of the object of measurement calculated respectively based on the data before and after the change are discrepant from each other by not less than a predetermined value.

Besides, the arithmetic unit according to the invention may determine measurement results through mean values of optical characteristics based on the data before and after the change of beam positions when the optical characteristics of the object of measurement calculated respectively based on the data before and after the change are within predetermined values.

In addition, the arithmetic unit according to the invention may determine measurement results based on data obtained by synthesizing the data before and after the change, based on the data before and after the change of beam positions, when the optical characteristics of the object of measurement calculated respectively based on the data before and after the change are within predetermined values.

Further, the present invention may resides in that the object of measurement is an eye under examination, the at least one surface of the object of measurement is the cornea surface, the first illumination optical system illuminates the cornea, the first light receiving optical system receives light through the first transforming member for transforming the luminous flux reflected by the cornea surface into at least nine beams, and the arithmetic unit can determine the shape of the cornea of the dye under examination as optical characteristics of the object.

Besides, the present invention may resides in that the object of measurement is an eye under examination, the at least one surface of the object of measurement is the retina, the first illumination optical system illuminates the retina, the first light receiving system receives light through the first transforming member for transforming the luminous flux reflected by the retina into at least nine beams, and the arithmetic unit can determine the refracting power of the eye under examination as optical characteristic of the object.

In addition, the present invention may resides in that the object of measurement is an optical lens, the first illumination optical system illuminates an illumination luminous flux such as to transmit through or be reflected by the optical lens, and the first light receiving optical system can receive light through the first transforming member for transforming the illumination luminous flux having transmitted through or been reflected by the optical lens into at least nine beams.

Further, the present invention may resides in that at least two kinds of the first transforming member are provided, a changeover from one of the first transforming members to the other of the first transforming members is carried out by linear movement or rotational movement, and the first transforming member thus changed over can be inserted into an optical path.

BEST MODE FOR CARRYING OUT THE INVENTION

Figure 1:
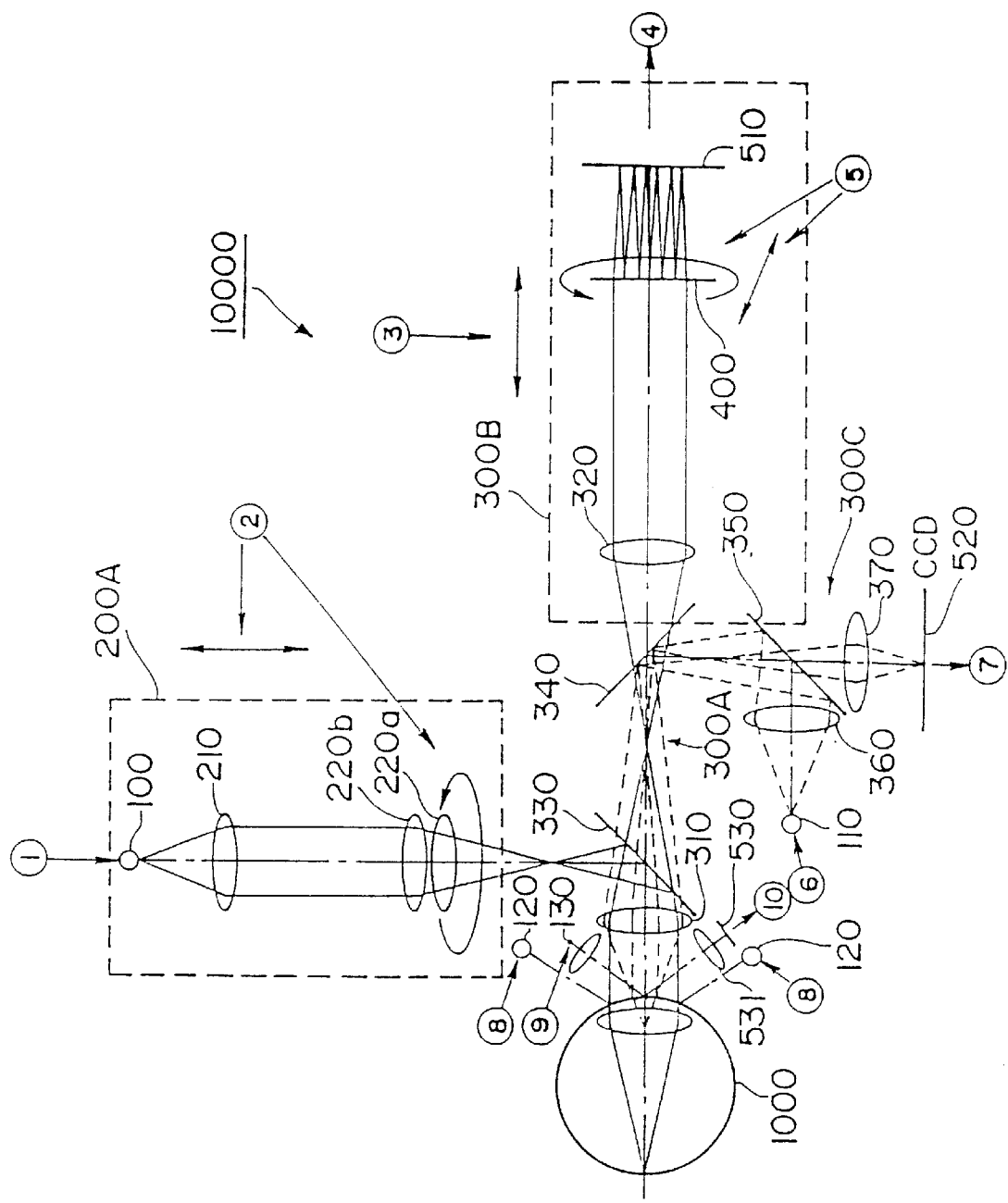
FIG. 1 is a diagram showing the constitution of an optical characteristic measuring apparatus 10000 according to First Embodiment of the present invention.

Now, embodiments of the present invention will be described referring to the drawings.

First Embodiment

Figure 2:
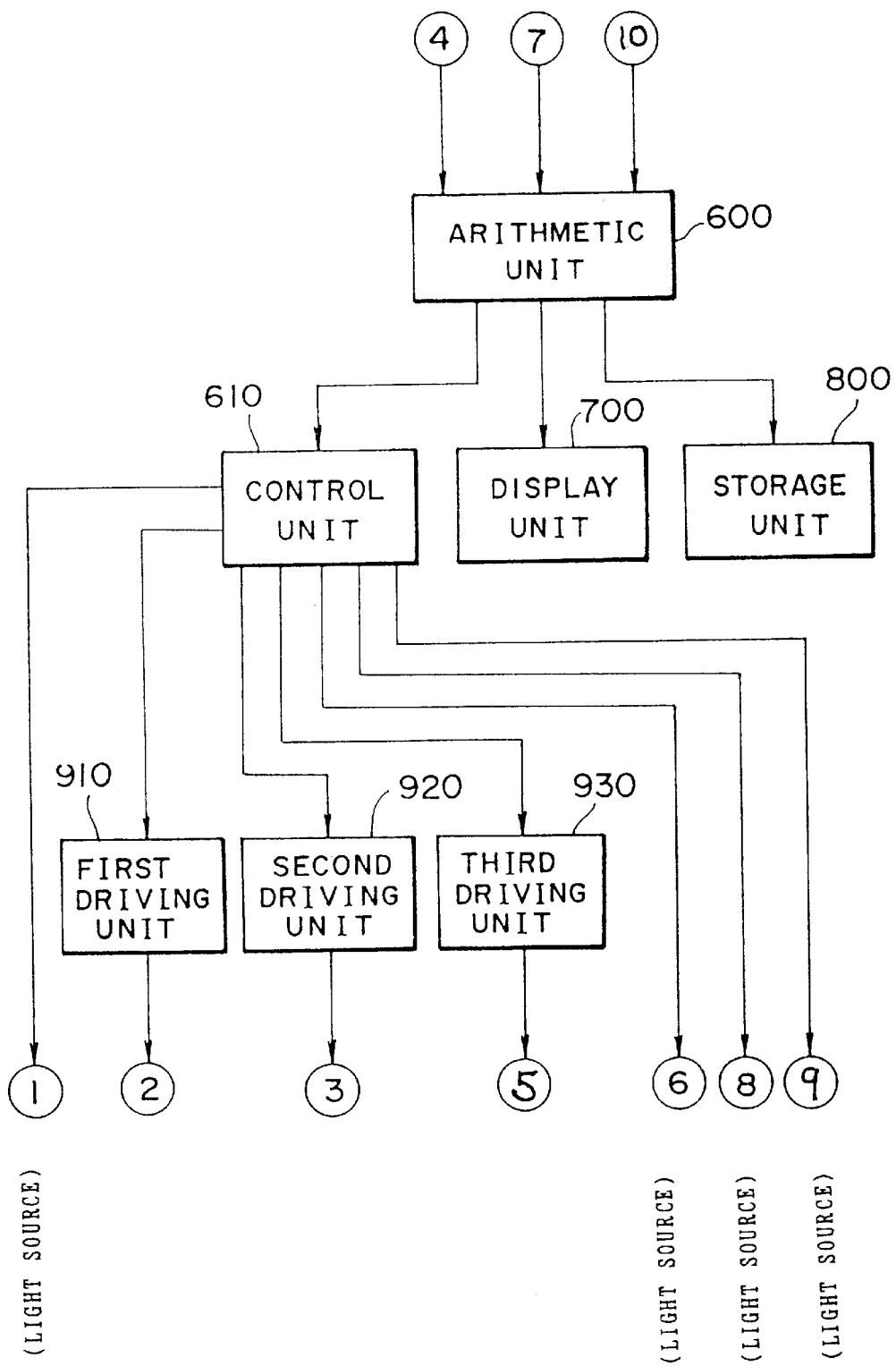
FIG. 2 is a diagram showing the electrical constitution of the optical characteristic measuring apparatus 10000 according to First Embodiment.

An eye characteristic measuring apparatus 10000 which is First Embodiment of the present invention, as shown in FIGS. 1 and 2, comprises a first light source unit 100 for emitting a luminous flux of a first wavelength, a first illumination optical system 200A for illuminating a minute area on the retina of an eye under examination with the luminous flux from the first light source unit 100 so that illumination conditions can be varied, a first light receiving optical system 300A for leading a portion of the luminous flux reflected back from the retina of the eye under examination to a first light receiving unit 510 through a first transforming member 400 for transforming the reflected luminous flux into at least nine beams, a second light receiving optical system 300B for leading a second luminous flux reflected back from the retina of the eye under examination to a second light receiving unit 520, and an arithmetic unit 600 for determining optical characteristics of the eye under examination based on a first signal from the first light receiving unit 510 corresponding to the angle of inclination of the luminous flux.

The arithmetic unit 600 performs control of the whole system including a control unit 610. Further, the control unit 610 receives signals ④, ⑦, ⑩ from the first light receiving unit 510, the second light receiving unit 520 and a third light receiving unit 530, controls the driving of the first light source unit 100 to a fourth light source unit 140 and the driving of a first driving unit 910 to a third driving unit 930, and controls a display unit 700 and a memory 800.

The first light source unit 100 is preferably one of which spatial coherence is high and time coherence is not high. As the first light source unit 100 in First Embodiment, an SLD is adopted, whereby a point light source with a high luminance can be obtained.

The first light source unit 100 in First Embodiment is not limited to the SLD; for example, a light source with high spatial coherence and high time coherence such as laser can also be utilized by appropriately lowering the time coherence by inserting a rotary diffuser plate or the like.

Also, a light source of which spatial and time coherences are not high, such as LED, can be used if only the light quantity is sufficient, by inserting a pin hole or the like at the position of a light source in an optical path.

As the wavelength of the first light source unit 100 for illumination in First Embodiment, a wavelength in the infrared region, for example, 780 nm can be used.

The first illumination optical system 200A is for illuminating a minute area on the retina of the eye under examination with the luminous flux from the first light source unit 100. The first illumination optical system 200A causes a luminous flux to pass through a first collimator lens 210 and a first condenser lens 220*b*, compensates for the astigmatism of the eye under examination by a cylindrical lens 220*a*, then once converges the luminous flux, and illuminates the eye under examination through an objective lens 310.

The first light receiving optical system 300A is for receiving the luminous flux reflected back from the retina of the eye under examination and leading it to the first light receiving unit 510. The first light receiving optical system 300A is constituted of a first afocal lens 310 and a light receiving unit 300B. The light receiving unit 300B is constituted of a second collimator lens 320, a first beam splitter 330, and a transforming member 400 for transforming the reflected luminous flux into at least nine beams.

The first beam splitter 330 is inserted in the first light receiving optical system 300A, whereby the light from the first illumination optical system 200A is fed to the eye 1000 under examination, and the reflected light is made to transmit through the first beam splitter 330.

The first light receiving unit 510 is for receiving the light from the first light receiving optical system 300A having passed through the transforming member 400, and generating a first signal.

The first light source unit 100 and the retina are conjugate, and the retina and the first light receiving unit 510 are conjugate. Further, the transforming member 400 and the pupil are conjugate.

Namely, the front side focus of the first afocal lens 310 roughly coincides with the anterior ocular segment of the eye under examination which is an object of examination.

Assuming that the luminous flux from the first light source unit 100 is reflected at the point where it condenses, the first illumination optical system 200A and the first light receiving optical system 300A are moved in conjunction with each other while maintaining such a relation that the signal peak at the first light receiving unit 510 due to the reflected light is maximized, are moved in such a direction that the signal peak at the first light receiving unit 510 becomes stronger, and are stopped at the position where the intensity of the signal peak is maximum. As a result, the luminous flux from the first light source unit 100 is condensed at the eye under examination.

Next, the transforming member 400 will be described.

The transforming member 400 disposed in the first light receiving optical system 300A is a wave front transforming member for transforming the reflected luminous flux into a plurality of beams. As the transforming member 400 in this First Embodiment, a plurality of micro-Fresnel lenses disposed on a plane orthogonal to the optical axis are adopted.

Figure 3:
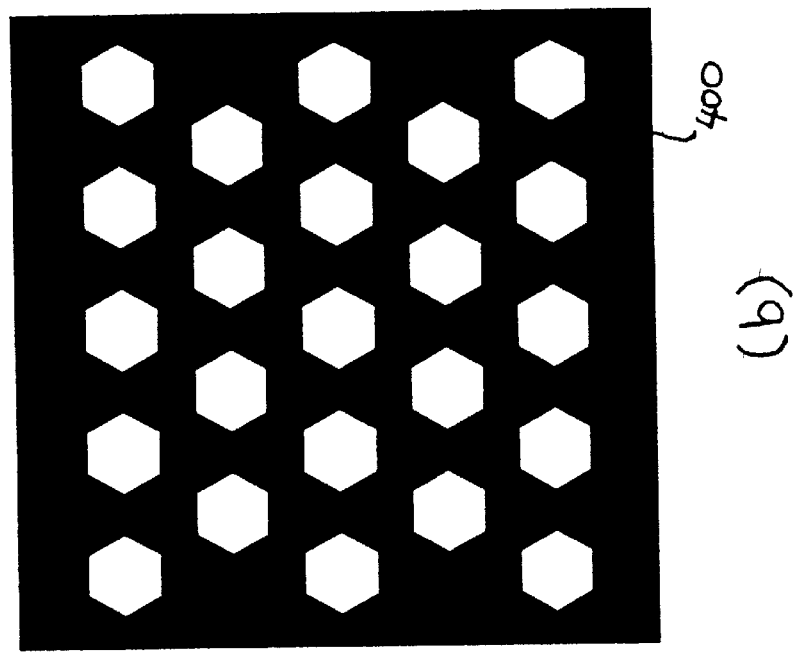
FIG. 3 illustrates the opening of a Hartmann plate.
Figure 3:
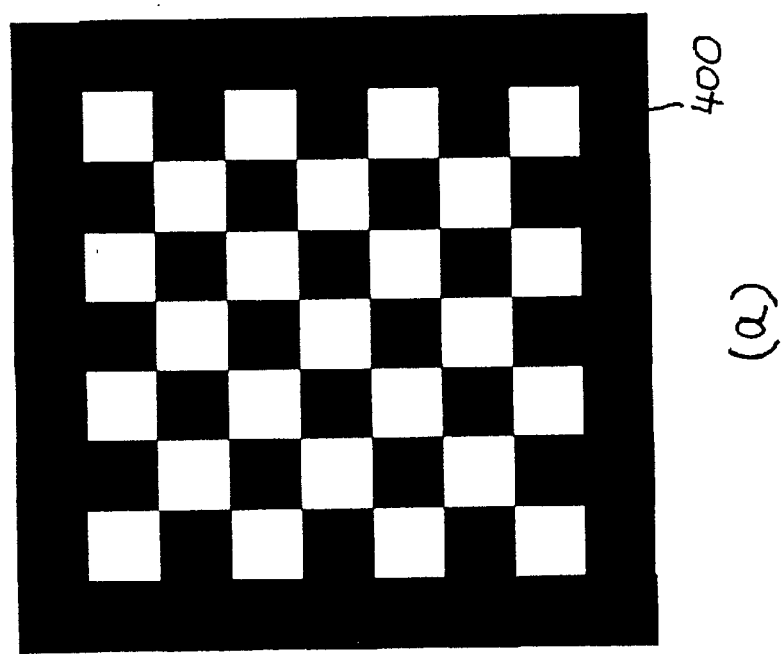

In order to measure the object of measurement up to other higher-order aberrations than third-order non-point aberration and spherical components, it is necessary to measure with at least 17 beams through the object of measurement. Therefore, in order to form at least 17 beams by moving the transforming member, it suffices that the transforming member is transformed into at least nine beams and measurement is carried out with a total of 18 beams before and after the movement. Examples of the transforming member are shown in FIGS. 3a and 3b. In both cases, the opening at the center is disposed in accord with the optical axis of the optical system.

Now, the micro-Fresnel lens will be described in detail.

The micro-Fresnel lens is an optical element which has ring bands of height pitches for each wavelength, and has blaze optimized for emission parallel to condensing points. The micro-Fresnel lens applicable here is, for example, provided with eight levels of optical path differences by applying semiconductor micro-fabrication technology, whereby a condensing efficiency of 98% can be realized.

The reflected light from the eyeground passes through the first afocal lens 310 and a second cylindrical lens 320, and condenses on the first light receiving unit 510 through the transforming member 400.

The transforming member 400 can also be constituted of a microlens portion for converging action and an opening portion for transmission action, in each of at least nine regions into which it is divided.

The transforming member 400 in this First Embodiment is constituted of a wave front transforming member for transforming the reflected luminous flux into at least nine beams.

Next, the first light receiving unit 510 is for receiving a plurality of beams transformed at the transforming member 400, and CCD with little read-out noise is adopted in this First Embodiment. As the CCD, any of the range from low noise type general ones to cooled CCD with 2000*2000 elements for measurement can be used.

The low noise type CCD and an image signal output from a driver thereof can be easily realized by using an adapted image input board.

The first light receiving optical system 300A has a roughly conjugate relation with the iris of the eye under examination and the transforming member 400.

In addition, the first beam splitter 330 is inserted in the light receiving optical system 300, whereby the light from the illumination optical system 200 is fed to the eye 1000 under examination, and the reflected light is made to transmit therethrough.

Further, an operating distance adjustment optical system for adjusting the operating distance between the eye 1000 under examination as the object and the optical characteristic measuring apparatus 10000, an alignment optical system for adjustment of positional relationship in directions orthogonal to the optical axis of the eye 1000 as the object and the optical characteristic measuring apparatus 10000, and a second illumination optical system for illuminating the object, are provided.

The alignment is carried out as follows. The luminous flux from the second light source unit 110 is made to pass through a condenser lens 370, beam splitters 350, 340 and the objective lens 310 so as to illuminate the eye 1000 under examination as the object with a roughly parallel luminous flux. The reflected luminous flux reflected by the cornea of the eye under examination is ejected in the form of a diverging luminous flux appearing as though it were ejected from a point of ½ of the radius of curvature of the cornea. The diverging luminous flux is transmitted through the objective lens 310, the beam splitters 350, 340 and the condenser lens 370 to be received as a spot image by the second light receiving unit 520. When the spot image is staggered from the optical axis on the second light receiving unit 520, the main body of the optical characteristic measuring apparatus 10000 is adjustingly moved upward, downward, leftward or rightward so as to bring the spot image onto the optical axis. When the spot image has come onto the optical axis on the second light receiving unit 520, the alignment adjustment is completed.

The wavelength at the second light source unit 110 is different from the wavelength at the first light source unit 100, and a longer wavelength, for example, 940 nm can be selected.

The beam splitter 340 may be composed of such a dichroic mirror as to transmit the wavelength at the first light source unit 100 but reflect the wavelength at the second light source unit 110, whereby it is possible to prevent the situation where the luminous flux in one of the optical systems comes into the other of the optical systems to constitute noise.

When the spot image has come onto the optical axis, the alignment adjustment is completed. The alignment adjustment can also be carried out by a method in which the anterior ocular segment of the eye under examination is illuminated by a third light source unit 120, thereby forming an image of the eye on the second light receiving unit 520, and the image of the anterior ocular segment is utilized to bring the center of the pupil onto the optical axis.

Next, adjustment of operating distance is carried out by a method in which a parallel luminous flux in the vicinity of the optical axis emitted from a fourth light source unit 130 is illuminated toward the object, and the light reflected from the eye under examination as the object is received by the third light receiving unit 530 through a condenser lens 531. The third light receiving unit 530 may well be a unit capable of detecting variations in luminous flux position in a plane including the fourth light source unit 130, the optical axis and the third light receiving unit 530, and may be constituted of, for example, a unidimensional CCD or a position sensing device (PSD) disposed in the plane.

When the eye under examination is located at an appropriate operating distance, a spot image from the fourth light source unit 130 is formed on the optical axis of the third light receiving unit 530, and when the eye is staggered from the appropriate operating distance to the front side or the rear side, the spot image is formed on the upper side or the lower side of the optical axis, respectively.

Here, electrical constitution of the optical characteristic measuring apparatus 10000 will be described referring to FIG. 2. The electrical constitution of the eye characteristic measuring apparatus 10000 comprises an arithmetic unit 600, a control unit 610, a display unit 700, a memory 800, a first driving unit 910, a second driving unit 920, and a third driving unit 920.

The control unit 610 is for controlling the turning ON and OFF of the first light source unit 100, and controlling the first driving unit 910, the second driving unit 920 and the third driving unit 930, based on control signals from the arithmetic unit 600.

The first driving unit 910 is for moving the first illumination optical system 200A as a whole in the optical axis direction or adjustingly rotating a first cylindrical lens 220a of the first illumination optical system 200A around the optical axis, based on a signal inputted from the first light receiving unit 510 into the arithmetic unit 600. The first driving unit 910 is so constituted as to move and adjust the illumination optical system 200A by driving an appropriate lens-moving means.

The second driving unit 920 is for moving the light receiving optical system 300A as a whole in the optical axis direction, based on a signal inputted from the first light receiving unit 510 into the arithmetic unit 600. The second driving unit 920 is so constituted as to move and adjust the light receiving optical system 300A by driving an appropriate lens-moving means.

The third driving unit 930 is for rotating the transforming member 400 with the optical axis as a center or around an axis parallel to the optical axis or moving the transforming member 400 in a direction orthogonal to the optical axis, by driving an appropriate rotating or moving means, based on a control signal from the arithmetic unit 600. The third driving unit 930 and the appropriate rotating or moving means correspond to the position change unit.

Namely, the position change unit is for changing the positions of the beams transformed by the transforming member 400. The position change unit in the present embodiment corresponds to a unit composed of mechanical constitution.

Incidentally, the principle of rotating the transforming member 400 with the optical axis as a center or moving the transforming member 400 in a direction orthogonal to the optical axis will be described later.

Figure 4B:
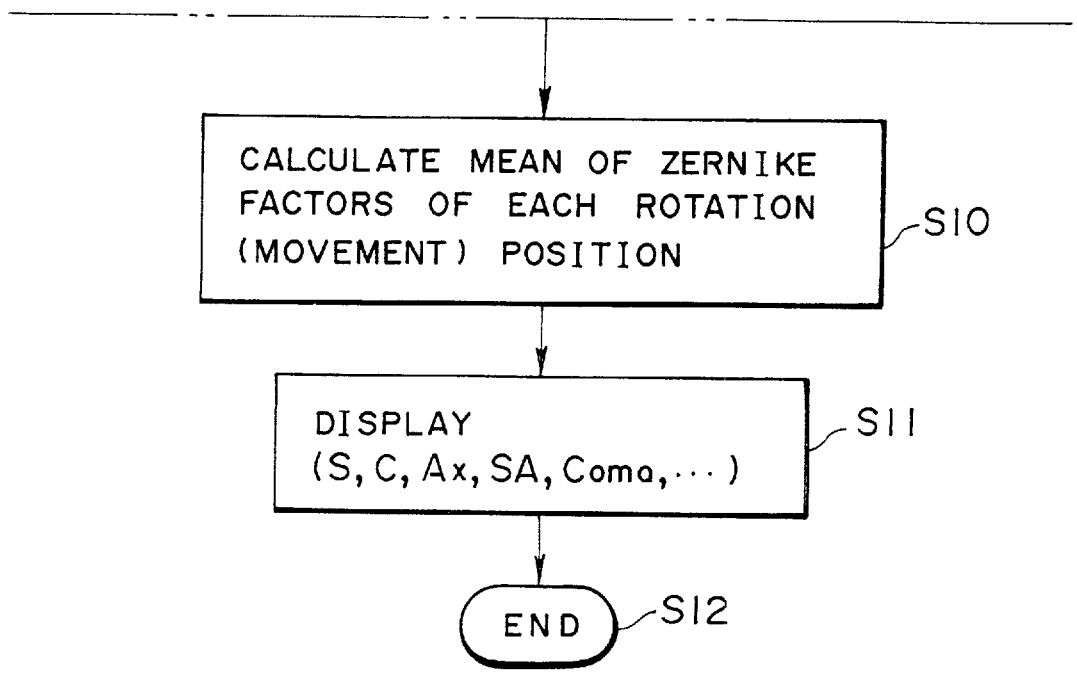
FIG. 4 is a diagram showing the operation of First Embodiment.

Next, a specific measuring method of the optical characteristic measuring apparatus 10000 will be described referring to FIG. 4.

In Step 1 (hereinafter abridged to S1), measurement is started. Next, in S2, image data is acquired from the first light receiving unit 510. A first check in S3 is to judge whether the object of measurement has moved before and after the movement of the transforming member 400, by observation of an image of the object on the second light receiving unit 520 or the like, or based on whether the light receiving position of a luminous flux having passed through the opening at the center of the transforming member 400 in the first light receiving optical system 300A has changed.

Figure 5:
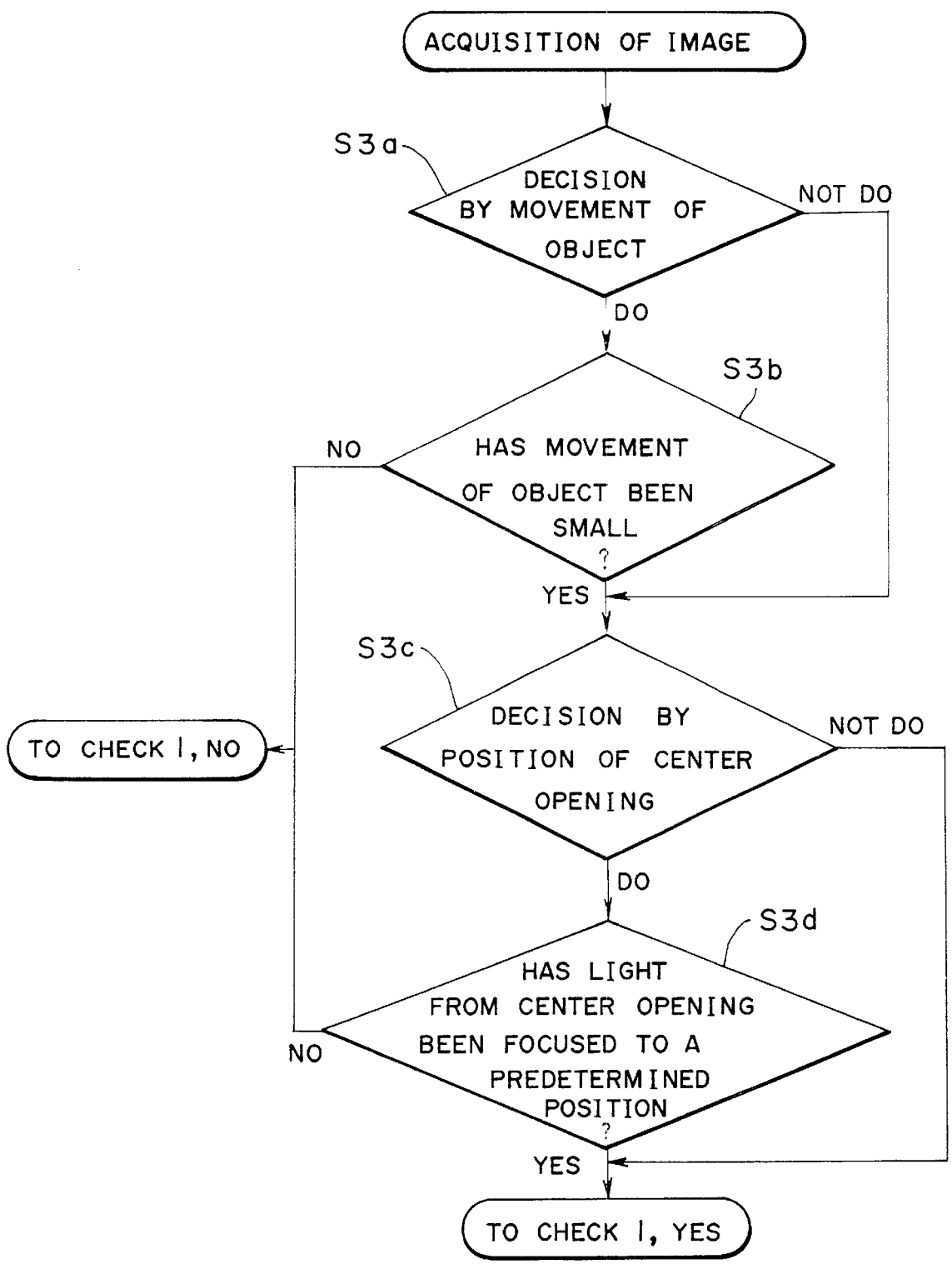
FIG. 5 is a diagram showing the operation of First Embodiment.

Here, the contents of S3 will be described referring to FIG. 5. First, in S3*a* it is judged whether decision by movement of the object is to be done or not; when the decision is to be done, S3*b* is entered, whereas when the decision is not to be done, S3*c* is entered. Namely, after the image is acquired in S2, whether decision of movement or non-movement of the object is to be done is judged in S3*a*. When the movement of the object is to be decided, in S3*b*, whether the spot image formed by the luminous flux reflected from the cornea of the eye under examination has been moved is judged by utilizing output signals from the second light receiving unit 520 before and after the measurement, and it is decided whether the movement amount is less than a predetermined value.

When it is decided in S3*b* that the movement amount of the object is larger than a predetermined value, the procedure returns to S2, where the image is again acquired, and the check in S3 is repeated.

When it is decided in S3*b* that the movement amount of the object is smaller than the predetermined value, S3*c* is entered. In S3*c*, it is judged whether decision of movement or non-movement of the object at the time of movement of the transforming member 400 (Hartmann plate) by use of a luminous flux having passed through the center opening of the transforming member 400 (Hartmann plate) is to be done.

In S3*c*, when the decision by center opening position is not to be done, the procedure goes to Check 1 YES, and when the decision is to be done, S3*d* is entered.

In S3*d*, decision is made by utilizing a luminous flux having passed through a member whose position is not changed before and after the movement of the transforming member 400, of the opening of the transforming member 400 and a lens portion. For example, when the transforming member 400 is rotated around an axis different from but parallel to the optical axis, a luminous flux passing through the opening portion located at the center of rotation can be utilized for decision, and when the transforming member 400 is brought into linear movement, a luminous flux passing through the opening whose position is the same before and after the change can be used for decision.

In S3*d*, it is judged whether the position of the luminous flux having passed through a predetermined opening has changed greatly before and after the movement of the transforming member; when the luminous flux position has changed greatly, the procedure returns to S2 (Check 1, No), where the image is again acquired, and the check in S3 is repeated. When, in S3*d*, the position of the luminous flux having passed through the predetermined opening has not changed greatly, S3' (Check 1, YES) is entered, where it is judged whether a predetermined number of sheets of data have been obtained.

When it is judged in S3*d*' that a predetermined number of sheets of data have been obtained, S4 is entered, where the position of center of gravity is detected. The gravity center position can be obtained, for example, by a method in which a luminous flux projected is projected onto a plurality of pixels on a light receiving surface, and the gravity center is determined taking the intensity of the luminous flux of each pixel as a reference. By calculating the center of gravity in this manner, precision of measurement position on the order of not more than ⅒ of the elements can be secured.

When it is judged in S3' that predetermined rotation data has not been obtained, S5 is entered, and the third driving unit 930 is driven to rotate or move the transforming member 400. Then, the procedure returns to S2.

Next, in S6, it is judged whether an image rotator 900 is to be used. When the image rotator 900 is not to be used, S7 is entered, where calculation of Zernike factor before and after the rotation or movement of the transforming member 400 is carried out. The calculation of the Zernike factor is carried out by the arithmetic unit 600 based on Expression (4) and Expression (5) which will be described later.

Here, the Zernike factor from the i-th image is made to be $(C_{nm})i$. In S7, $(C_{nm})i$ is calculated from all images.

When it is judged in S6 that the image rotator 900 is to be used, S8 is entered, where spot images are corrected by rotation or movement by utilizing the image rotator 900. The operation for correcting the spot images by rotation or movement by utilizing the image rotator 900 will be detailed in Modified Embodiment described later. In S8, the spot images are corrected by rotation with the optical axis as a center or by movement in a direction orthogonal to the optical axis, and thereafter S7 is entered.

In S7, Zernike factors (given by Expression (4) and Expression (5) described later) of each rotation (movement) position are calculated. When the calculation of the Zernike factors is finished, S9 is entered. In S9, movement of the eye 1000 under examination before and after the change of the transforming member 400 is judged based on the Zernike factors and from tilt components, spherical components and non-point aberration factors. When it is judged in S9 that the movement amount of the object is greater than a predetermined value, the procedure returns to S2, where images are again acquired, and the following treatments are repeated. When it is judged in S9 that the movement amount of the object is smaller than the predetermined value, S10 is entered, where the mean of Zernike factors of each rotation (or movement) position is calculated.

Figure 6B:
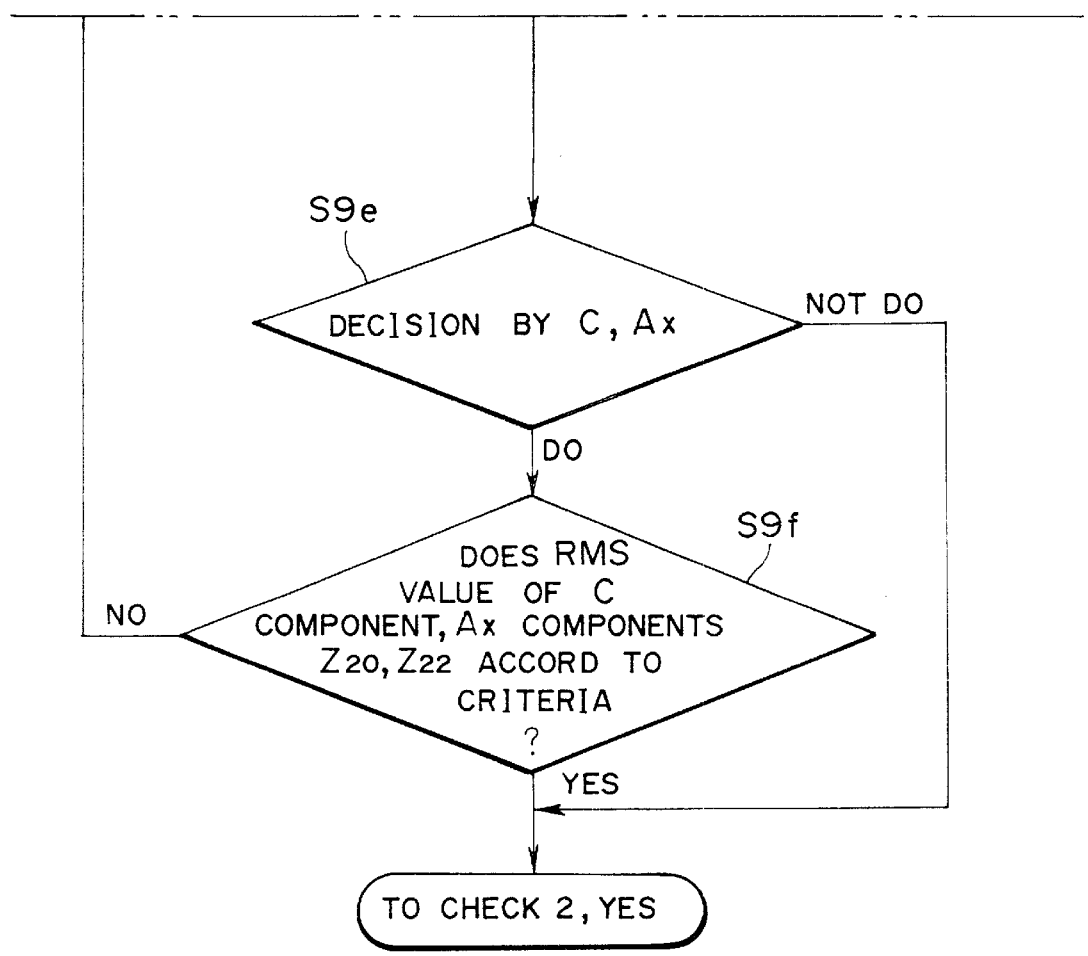
FIG. 6 is a diagram showing the operation of First Embodiment.

Here, the contents of the judgment in S9 is detailed referring to FIG. 6.

In S9a, it is judged whether decision of movement or non-movement of the object before and after the movement of the transforming member 400 based on the Zernike factors determined is to be done. When it is judged in S9a that the decision is to be done, S9b is entered, and when it is judged in S9a that the decision is not to be done, S9c is entered.

In S9b, the movement amount of the object which is a tilt component is judged by use of RMS value of Zernike terms $Z_{10}$, $Z_{11}$ representing the tilt components of Zernike factors $(C_{nm})i$. The factors in Zernike expansion are represented by $C_{ij}$. The factors of the Zernike terms $Z_{10}$ and $Z_{11}$ with respect to the tilt component are $C_{10}$ and $C_{11}$, and the RMS value of the sum is represented by:

$$RMS_1 = (C_{10}^2/4 + C_{11}^2/4)^{0.5}.$$

When it is judged in S9b that the tilt component is not within a predetermined value, the procedure returns to S2, where images are again acquired, and the following treatments are repeated. When it is judged in S9b that the tilt component is within the predetermined value, S9c is entered.

In S9c, it is judged based on the Zernike factors obtained whether decision of the spherical components of the object being or not being within a predetermined value before and after the movement of the transforming member 400 is to be done.

When it is judged in S9c that the decision is to be done, S9d is entered, and when it is judged in S9c that the decision is not to be done, S9e is entered.

In S9d, it is decided based on the Zernike factors obtained whether the spherical component of the object before and after the movement of the transforming member 400 is within a predetermined value.

The decision in S9d is carried out by judging the movement amount of the object which is the spherical component, by using the RMS value of the Zernike term $Z_{21}$ representing the spherical component, of the Zernike factors $(C_{nm})i$. The factors in Zernike expansion are represented by $C_{ij}$. The factor of the Zernike term $Z_{21}$ for the spherical component is $C_{21}$, and the RMS value of the sum is represented by:

$$RMS_{21} = C_{21}/3^{0.5}.$$

When it is decided in S9d that the spherical component is not within a predetermined value, the procedure returns to S2, where images are again acquired, and the following treatments are repeated. When it is decided in S9d that the spherical component is within the predetermined value, S9e is entered.

In S9e, it is judged based on the Zernike factors obtained whether decision of the non-point aberration component of the object being or not being within a predetermined value before and after the movement of the transforming member 400 is to be done. When it is judged in S9e that the decision is to be done, S9f is entered, and when it is judged in S9e that the decision is not to be done, S10 is entered.

In S9f, it is decided based on the Zernike factors obtained whether the non-point aberration component of the object is within a predetermined value before and after the movement of the transforming member 400.

In S9f, the RMS value (magnitude of cylindrical component) of the sum of Zernike terms $Z_{20}$ and $Z_{21}$ representing a cylindrical component (C) and a cylinder axis component $(A_x)$, of the Zernike factors $(C_{nm})i$, is determined.

Where the factors in Zernike expansion are $C_{ij}$, the factor of the Zernike term $Z_{20}$ for the cylindrical component is $C_{20}$, and the RMS value of the sum is represented by:

$$\text{Cylindrical component} = (C_{20}^2/6 + C_{22}^2/6)^{0.5}.$$

The cylinder axis component $(A_x)$ is represented by:

$$A_x = \tfrac{1}{2} \arctan(C_{20}/C_{22}).$$

When it is decided in S9f that the cylindrical component is not within a predetermined value, the procedure returns to S2, where images are again acquired, and the following treatments are repeated. When it is decided in S9f that the cylindrical component is within the predetermined value, S10 is entered.

In S10, the mean of Zernike factors at each rotation (or movement) position is calculated.

In S11, movement amounts of the first illumination optical system 200A as a whole and the light receiving unit 300B as well as S, C, $A_x$, SA, Coma and the like calculated from the Zernike polynomial are displayed at a display unit 700. After the calculation results are displayed in S11, S12 is entered, where the measurement is finished.

Modified Embodiment of Measuring Method of First Embodiment

Figure 7:
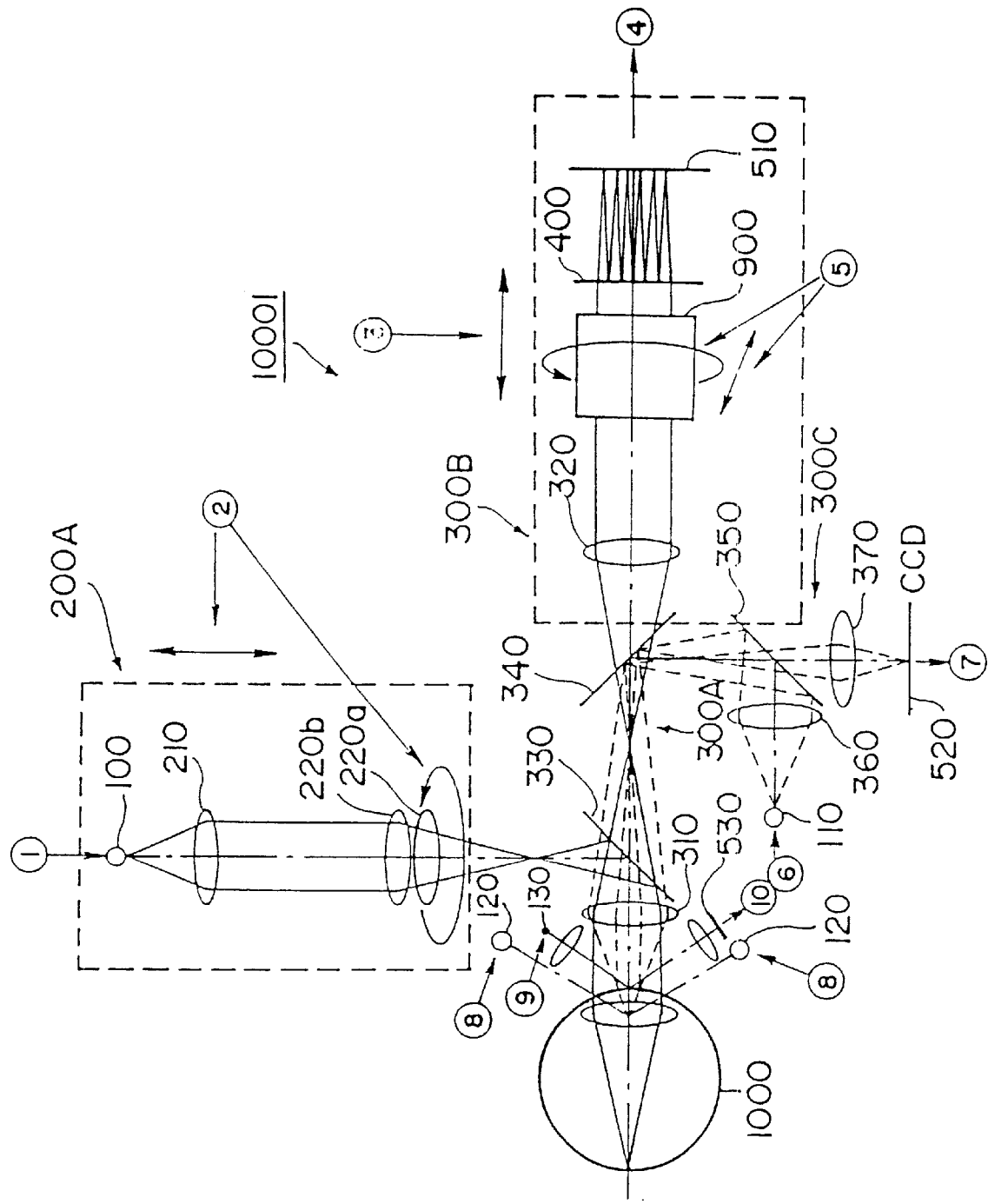
FIG. 7 is a diagram showing the constitution of an optical characteristic measuring apparatus 1001 according to a modified embodiment of First Embodiment.

An optical characteristic measuring apparatus 10001 which is Modified Embodiment of the First Embodiment, as shown in FIG. 7, comprises a first light source unit 100 for emitting a luminous flux of a first wavelength, a first illumination optical system 200A for illuminating a minute area on the retina of an eye under examination with the luminous flux from the first light source unit 100 so that the illumination conditions can be varied, a first light receiving optical system 300A for leading a portion of the luminous flux reflected back from the retina of the eye under examination to a first light receiving unit 510 through a first transforming member 400 for transforming the reflected luminous flux into at least nine beams, an arithmetic unit 600 for determining optical characteristics of the eye under examination based on a first signal from the first light receiving unit 510 corresponding to the angle of inclination of the luminous flux, and an image rotator 900.

The first light receiving optical system 300A is for receiving the luminous flux reflected back from the retina of the eye under examination and leading it to the first light receiving unit 510. The first light receiving optical system 300A is constituted of a first afocal lens 310, a first beam splitter 330, and a light receiving unit 300B. The light receiving unit 300B is constituted of a first collimator lens 320, the image rotator 900, and the transforming member 400 for transforming the reflected luminous flux into at least 17 beams.

The image rotator 900 is for rotating or moving spot images. In the present first modified embodiment, the image rotator 900 performs rotation or movement by an appropriate image rotator driving means.

Therefore, in place of the system so constituted as to rotate or move the transforming member 400 by the third driving unit 930, in this first Modified Embodiment, the third driving unit 930 controllingly drives the image rotator driving means based on a control signal from the arithmetic unit 600, thereby rotating or moving the image rotator 900. As the image rotator driving means, for example, a stepping motor, a piezo element or the like can also be utilized.

Then, the third driving unit 930 and the image rotator driving means correspond to a position transforming unit. In addition, the position change unit in the Modified Embodiment of the First Embodiment corresponds to an optical constitution.

The other aspects of constitution, action and the like are the same as in the First Embodiment, so that description thereof is omitted.

Second Embodiment

The optical constitution of Second Embodiment of the present invention is the same as that of First Embodiment, but the measuring method differs from that in the First Embodiment, and, therefore, a specific measuring method will be described in detail.

Figure 8B:
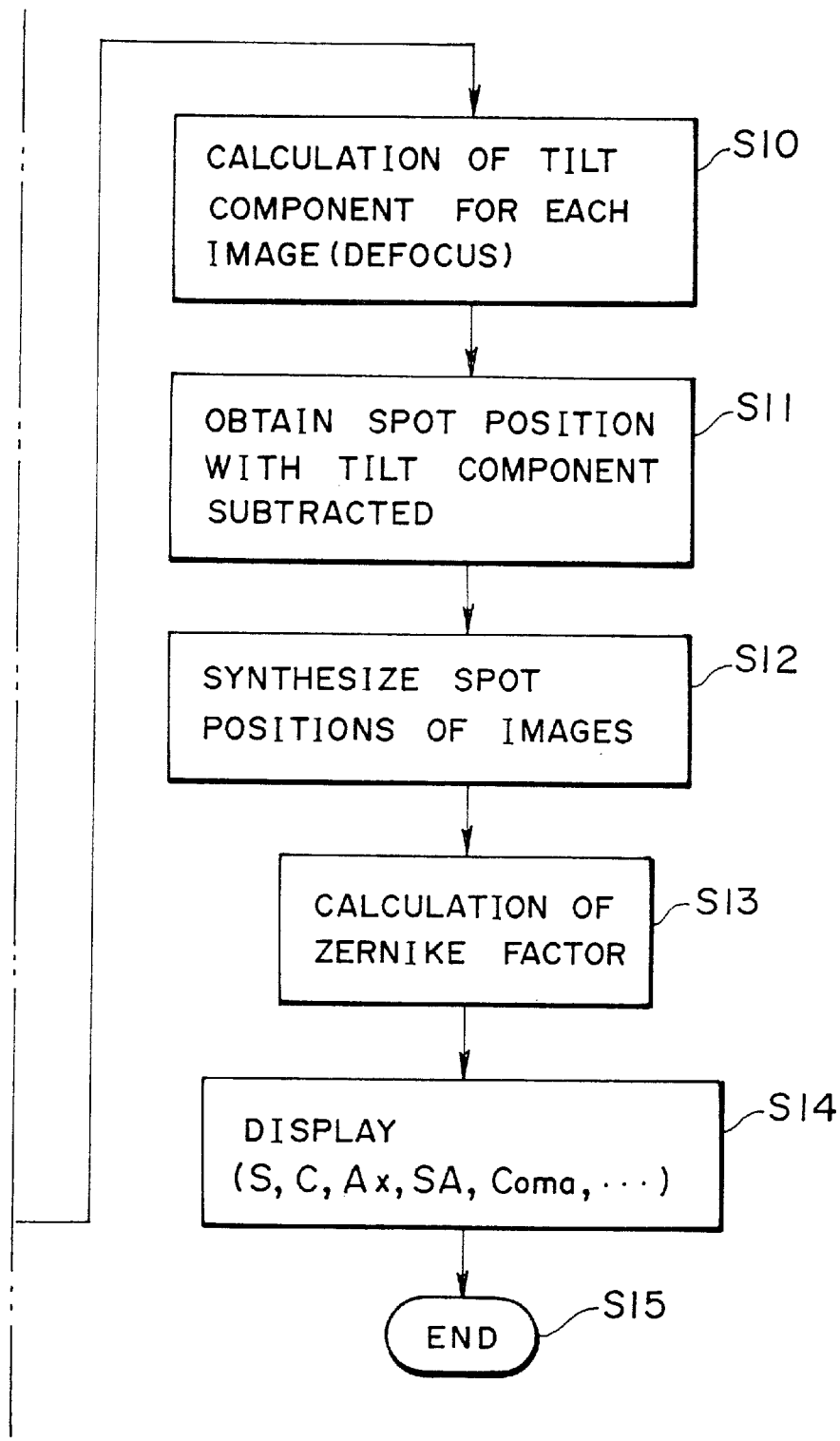
FIG. 8 is a diagram showing the operation of Second Embodiment.

Now, the specific measuring method according to Second Embodiment will be described referring to FIG. 8.

In Step 1 (hereinafter abridged to S1), measurement is started. Next, in S2, image data is acquired from a first light receiving unit 510. Then, in S3, it is judged whether predetermined rotation data has been obtained, and when the predetermined rotation data has been obtained, S4 is entered. In S4, the position of center of gravity is detected. The gravity center position can also be obtained by a method in which a luminous flux to be projected is projected onto a plurality of pixels on a light receiving surface, and the gravity center position is obtained taking the intensity of luminous flux of each pixel as a reference. By calculating the center of gravity in this manner, precision of measured positions on the order of not more than 1/10 of the elements can be secured.

When it is judged in S3 that the predetermined rotation data has not been obtained, S5 is entered, where the third driving unit 930 is driven to rotate or move the transforming member 400. Then, the procedure returns to S2.

Next, in S6, it is judged whether the image rotator 900 is to be used. When the image rotator 900 is not to be used, S7 is entered, where Zernike factors after the rotation or movement of the transforming member 400 are calculated. The calculation of the Zernike factors is performed by the arithmetic unit 600 based on Expression (4) and Expression (5) described later.

Here, the Zernike factor from i-th image is represented by $(C_{nm})i$. In S7, $(C_{nm})i$ are calculated from all images.

When it is judged in S6 that the image rotator 900 is to be used, S8 is entered, where spot images are corrected by rotation or movement by utilizing the image rotator 900. The operation of correcting the spot images through rotation or movement by utilizing the image rotator 900 will be detailed in a modified embodiment described later. After the spot images are corrected through rotation or movement in S8, S7 is entered.

In S7, Zernike factors (represented by Expression (4) and Expression (5) described later) at each rotation (movement) position are calculated. When the calculation of the Zernike factors is finished in S7, S9 is entered. In S9, the movement of the eye 1000 under examination before and after the change of the transforming member 400 is judged based on the Zernike factors and from tilt components, spherical components and non-point aberration factor. When it is judged in S9 that the movement amount of the object is greater than a predetermined value, the procedure returns to S2, where images are again acquired, and the following treatments are repeated. When it is judged in S9 that the movement amount of the object is smaller than the predetermined value, S10 is entered, where tilt components (defocus) of each image are calculated.

In S9a, it is judged whether decision of movement or non-movement of the object before and after the movement of the transforming member 400 is to be done, based on the Zernike factors obtained. When it is judged in S9a that the decision is to be done, S9b is entered, and when it is judged in S9a that the decision is not to be done, S9c is entered.

In S9b, the movement amount of the object which is a tilt component is judged by use of the RMS value of Zernike factors $Z_{10}$, $Z_{11}$ representing the tilt component, of the Zernike factors $(C_{nm})i$. The factors in Zernike expansion are represented by $C_{ij}$. The factors of the Zernike terms $Z_{10}$, $Z_{11}$ for the tilt component are $C_{10}$, $C_{11}$, and the RMS value of the sum is represented by:

$$RMS_1 = (C_{10}^2/4 + C_{11}^2/4)^{0.5}.$$

When it is decided in S9b that the tilt component is not within a predetermined value, the procedure returns to S2, where images are again acquired, and the following treatments are repeated. When it is decided in S9b that the tilt component is within the predetermined value, S9c is entered.

In S9c, it is judged based on the Zernike factors obtained whether decision of the spherical component of the object being or not being within a predetermined value before and after the movement of the transforming member 400 is to be done.

When it is judged in S9c that the decision is to be done, S9d is entered, and when it is judged in S9c that the decision is not to be done, S9e is entered.

In S9d, it is decided based on the Zernike factors obtained whether the spherical component of the object is within the predetermined value before and after the movement of the transforming member 400.

The decision in S9d is carried out by judging the movement amount of the object which is the spherical component by use of the RMS value of the Zernike term $Z_{21}$ representing the spherical component, of the Zernike factors $(C_{nm})i$. The factors in Zernike expansion are represented by $C_{ij}$. The factor of the Zernike term $Z_{21}$ for the spherical component is $C_{21}$, and the RMS value of the sum is represented by:

$$RMS_{21} = C_{21}/3^{0.5}.$$

When it is decided in S9d that the spherical component is not within the predetermined value, the procedure returns to S2, where images are again acquired, and the following treatments are repeated. When it is decided in S9d that the spherical component is within the predetermined value, S9e is entered.

In S9e, it is judged based on the Zernike factors obtained whether decision of the non-point aberration component of the object being or not being within a predetermined value before and after the movement of the transforming member 400 is to be done. When it is judged in S9e that the decision is to be done, S9f is entered, and when it is judged in S9e that the decision is not to be done, S10 is entered.

In S9f, it is decided based on the Zernike factors obtained whether the non-point aberration component of the object is within a predetermined value before and after the movement of the transforming member 400.

In S9f, the RMS value (the magnitude of the cylindrical component) of the sum of Zernike terms $Z_{20}$ and $Z_{22}$ representing a cylindrical component (C) and a cylinder axis component $(A_x)$, of the Zernike factors $(C_{nm})i$, is determined.

When the factors in Zernike expansion are represented by $C_{ij}$, the factor of the Zernike term $Z_{20}$ for the cylindrical component is $C_{20}$, and the RMS value of the sum is represented by:

$$\text{Cylindrical component} = (C_{20}^2/6 + C_{22}^2/6)^{0.5}.$$

The cylinder axis component $(A_x)$ is represented by:

$$A_x = \tfrac{1}{2} \arctan(C_{20}/C_{22}).$$

When it is decided in S9f that the cylindrical component is not within a predetermined value, the procedure returns to S2, where images are again acquired, and the following treatments are repeated. When it is decided in S9f that the cylindrical component is within the predetermined value, S10 is entered.

In S10, the mean of Zernike factors at each rotation (movement) position is calculated.

Then, in S11, the positions of the spots with the tilt component (defocus) subtracted are determined. By this, the position of center of gravity can be corrected. Next, in S12, the spot positions are synthesized.

Further, in S13, Zernike factors are calculated by utilizing all points. The zernike factors are calculated by the arithmetic unit 600 based on Expression (4) and Expression (5) described later.

Then, in S14, the movement amounts of the first illumination optical system 200A as a whole and a light receiving unit 300B as well as S, C, $A_x$, SA, Coma and the like calculated from the Zernike polynomial are displayed at a displayunit 700. After displaying the calculation results in S15, S12 is entered, where the measurement is finished.

The other aspects of constitution, action and the like are the same as in First Embodiment, so that the description thereof is omitted.

Third Embodiment

The optical constitution of Third Embodiment of the present invention is the same as that of First Embodiment, but the measuring method of the Third Embodiment differs from that of First Embodiment, and, therefore, the specific measuring method will be detailed below.

Figure 9B:
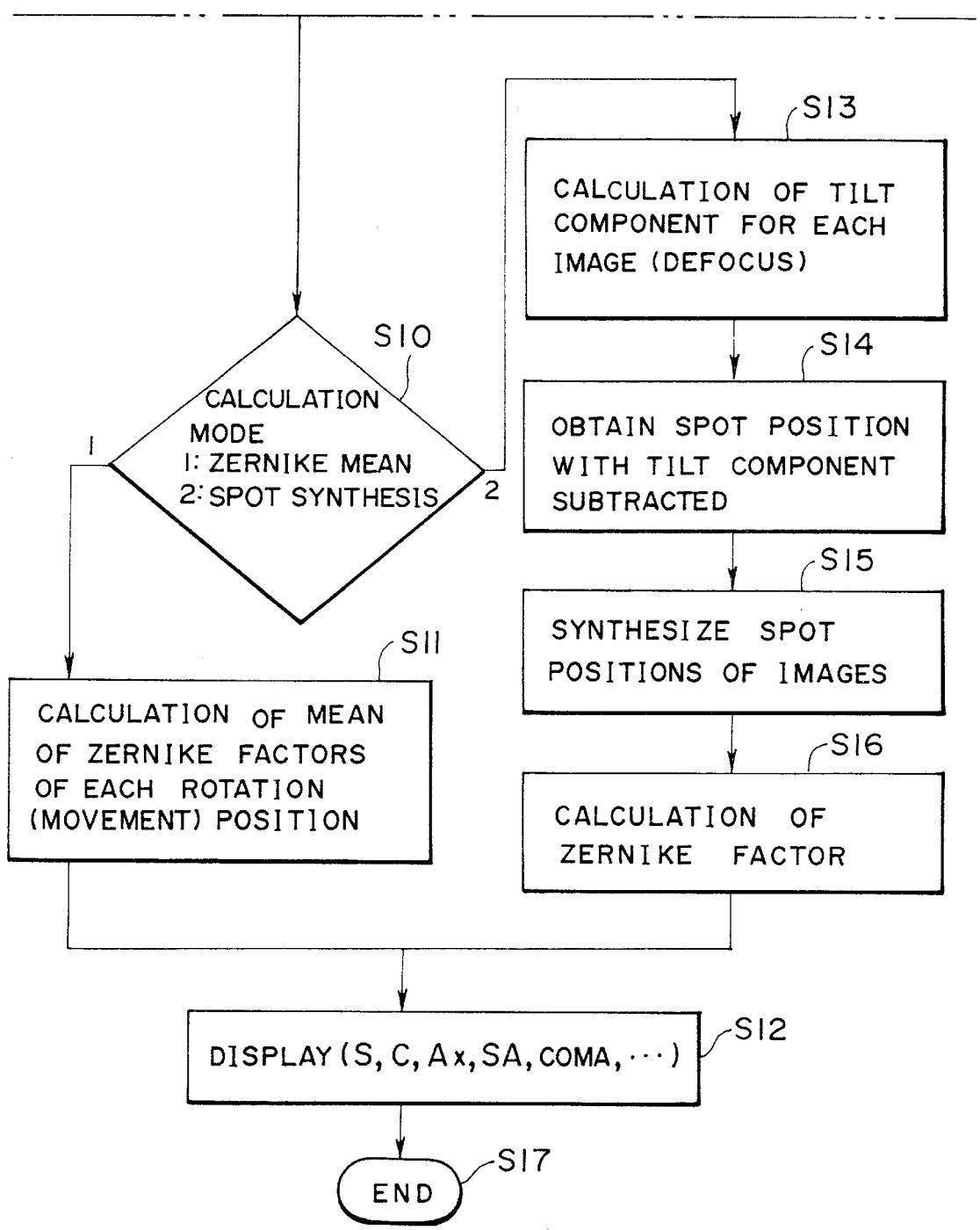
FIG. 9 is a diagram showing the operation of Third Embodiment.

Now, the specific measuring method according to Third Embodiment will be described referring to FIG. 9.

In Step 1 herein after abridged to S1), measurement is started. Next, in S2, image data is acquired from a first light receiving unit 510. Then, in S3, it is judged whether predetermined rotation data has been obtained, and when the predetermined rotation data has been obtained, S4 is entered. In S4, the position of center of gravity is detected. The gravity center position can also be obtained by, for example, a method in which a luminous flux projected is projected onto a plurality of pixels on a light receiving surface, and the gravity center position is determined taking the intensity of luminous flux of each pixel as reference. By calculating the center of gravity in this manner, precision of measured position on the order of not more than $\tfrac{1}{10}$ of the elements can be secured.

When it is judged in S3 that the predetermined rotation data has not been obtained, S5 is entered, where a third driving unit 930 is driven to rotate or move a transforming unit 400. Then, the procedure returns to S2.

Next, in S6, it is judged whether an image rotator 900 is to be used. When the image rotator 906 is not to be used, S7 is entered, where Zernike factors after the rotation or movement of the transforming unit 400 are calculated. The calculation of the Zernike factors is carried out by an arithmetic unit 600 based on Expression (4) and Expression (5) described later.

Here, the Zernike factor from the i-th image is represented by $(C_{nm})i$. In S7, $(C_{nm})i$ are calculated from all images.

When it is judged that the image rotator 900 is to be used, S8 is entered, where spot images are corrected through rotation or movement by utilizing the image rotator 900. The operation of correcting the spot images through rotation or movement will be detailed in a modified embodiment described later. After the spot images are corrected through rotation or movement in S8, S7 is entered.

In S7, Zernike factors (represented by Expressions (4) and (5) described later) at each rotation (movement) position are calculated. When calculation of the Zernike factors in S7 is completed, S9 is entered. In S9, movement of the eye 1000 under examination before and after the change of the transforming unit 400 is judged from tilt component, spherical component and non-point aberration factor, based on the Zernike factors. When it is judged in S9 that the movement amount of the object is greater than a predetermined value, the procedure returns to S2, where images are again acquired, and the following treatments are repeated. When it is judged in S9 that the movement amount of the object is smaller than the predetermined value, S10 is entered, where selection of calculation mode is conducted. In S10, selection of (1) Zernike mean mode and (2) spot synthesis mode is carried out.

In S9a, it is judged based on the Zernike factors obtained whether decision of movement or non-movement of the object before and after the movement of the transforming unit 400 is to be done. When it is judged in S9a that the decision is to be done, S9b is entered, and when it is judged in S9a that the decision is not to be done, S9c is entered.

In S9b, the movement amount of the object which is the tilt component is judged by use of the RMS value of Zernike factors $Z_{10}$, $Z_{11}$ representing the tilt components, of the Zernike factors $(C_{nm})i$. The factors in Zernike expansion are represented by $C_{ij}$. The factors of the Zernike terms $Z_{10}$, $Z_{11}$ for the tilt component are $C_{10}$, $C_{11}$, and the RMS value of the sum is represented by:

$$RMS_1 = (C_{10}^2/4 + C_{11}^2/4)^{0.5}.$$

When it is judged in S9b that the tilt component is not within a predetermined value, the procedure returns to S2, where images are again acquired, and the following treatments are repeated. When it is judged in S9b that the tilt component is within the predetermined value, S9c is entered.

In S9c, it is judged based on the Zernike factors obtained whether decision of the spherical component of the object being or not being within a predetermined value before and after the movement of the transforming unit 400 is to be done.

When it is judged in S9c that the decision is to be done, S9d is entered, and when it is judged in S9c that the decision is not to be done, S9e is entered.

In S9d, it is decided based on the Zernike factors obtained whether the spherical component of the object is within a predetermined value before and after the movement of the transforming unit 400.

The decision in S9d is carried out by judging the movement amount of the object which is the spherical component by use of the RMS value of the Zernike factor $Z_{21}$ representing the spherical component, of the Zernike factors $(C_{nm})i$. The factors in Zernike expansion are represented by $C_{ij}$. The factor of the Zernike term $Z_{21}$ for the spherical component is $C_{21}$, and the RMS value of the sum is represented by:

$$RMS_{21} = C_{21}/3^{0.5}.$$

When it is judged in S9d that the spherical component is not within a predetermined value, the procedure returns to S2, where images are again acquired, and the following treatments are repeated. When it is judged in S9d that the spherical component is within the predetermined value, S9e is entered.

In S9e, it is judged based on the Zernike factors obtained whether decision of the non-point aberration component of the object being or not being within a predetermined value before and after the movement of the transforming unit 400 is to be done. When it is judged in S9e that the decision is to be done, S9f is entered, and when it is judged in S9e that the decision is not to be done, S10 is entered.

In S9f, it is decided based on the Zernike factors obtained whether the non-point aberration component of the object is within a predetermined value before and after the movement of the transforming unit 400.

Then, in S9f, the RMS value (magnitude of cylindrical component) of the sum of Zernike terms $Z_{20}$ and $Z_{22}$ representing a cylindrical component (C) and a cylinder axis component $(A_x)$, of the Zernike factors $(C_{nm})i$, is determined.

Where the factors in Zernike expansion are represented by $C_{ij}$, the factor of the Zernike term $Z_{20}$ for the cylindrical component is $C_{20}$, and the RMS value of the sum is represented by:

$$\text{Cylindrical component} = (C_{20}^2/6 + C_{22}^2/6)^{0.5}.$$

The cylinder axis component $(A_x)$ is represented by:

$$A_x = \tfrac{1}{2} \arctan (C_{20}/C_{22}).$$

When it is decided in S9f that the cylindrical component is not within a predetermined value, the procedure returns to S2, where images are again acquired, and the following treatments are repeated. When it is decided in S9f that the cylindrical component is within the predetermined value, S10 is entered.

When (1) Zernike mean mode is selected in S10, S11 is entered, where the mean of the Zernike factors of each rotation (movement) position is calculated. After the mean of the Zernike factors is calculated in S11, S12 is entered, where the movement amounts of a first illumination optical system 200A as a whole and a light receiving unit 300B as well as S, C, $A_x$, SA, Coma and the like calculated from Zernike polynomial are displayed at a display unit 700.

When (2) spot synthesis mode is selected in S10, S13 is entered, where the tilt component (defocus) of each image is calculated.

Then, in S14, the positions of spots with the tilt component (defocus) subtracted are determined. By this, correction of the position of the center of gravity can be carried out. Next, in S15, each spot position is synthesized.

Further, in S16, calculation of Zernike factors is carried out by utilizing all points. The Zernike factors are calculated by an arithmetic unit 600 based on Expressions (4) and (5) which will be described later.

After the Zernike factors are calculated in S15, S12 is entered, where the movement amounts of the first illumination optical system 200A as a whole and the light receiving unit 300B as well as S, C, $A_x$, SA, Coma and the like calculated from the Zernike polynomial are displayed at the display unit 700. After the calculation results are displayed in S12, S17 is entered, where the measurement is finished.

The other aspects of constitution, action and the like are the same as in First Embodiment, so that the description thereof is omitted.

Fourth Embodiment

Figure 10:
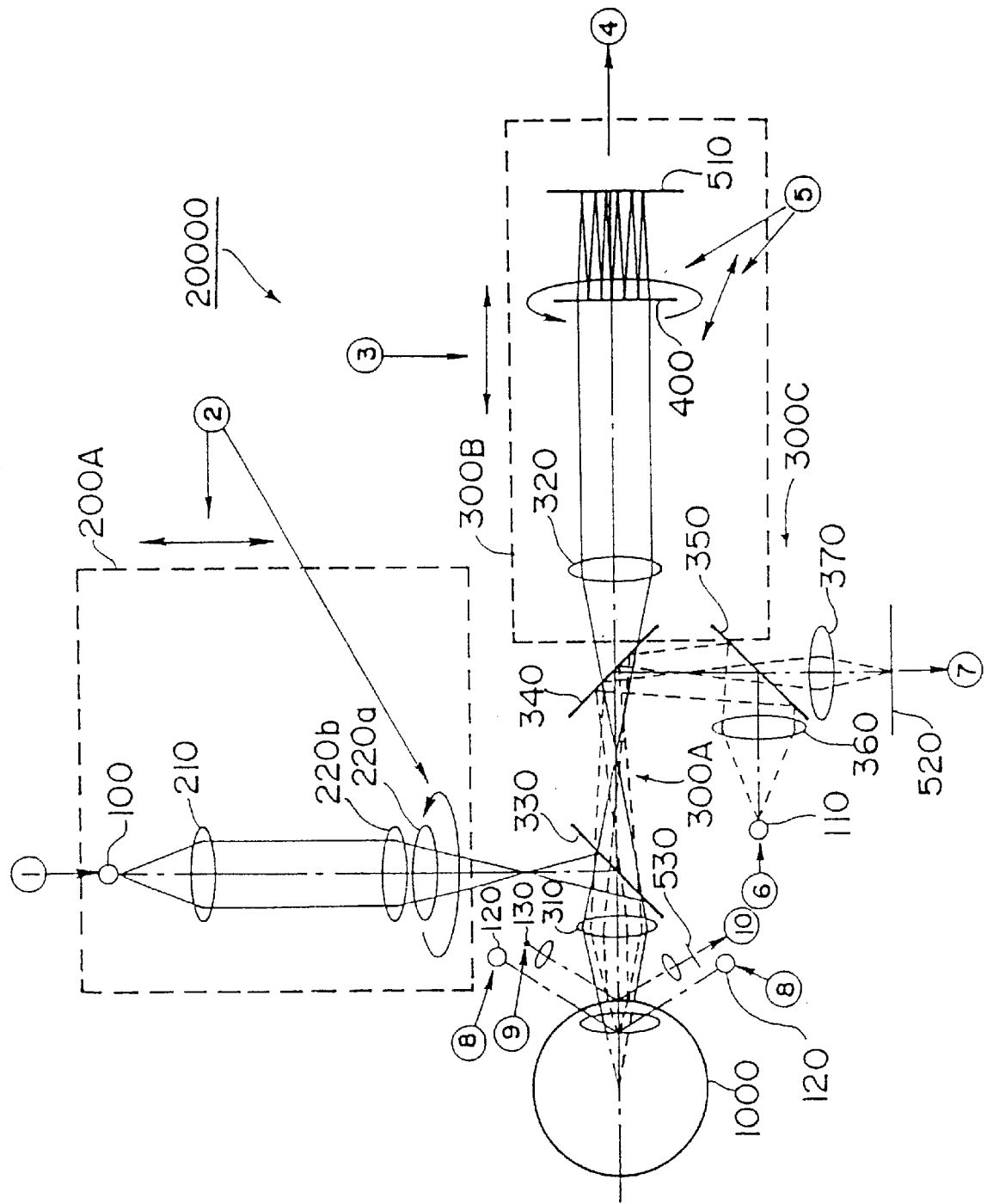
FIG. 10 is a diagram illustrating the optical constitution of an optical characteristic measuring apparatus 20000 according to Fourth Embodiment.

An optical characteristic measuring apparatus 20000 according to Fourth Embodiment of the present invention has an optical constitution in the case of measuring a cornea. As shown in FIG. 10, the optical constitution is the same as that in First Embodiment, and is so arranged that the cornea can be measured.

Referring to FIG. 10, the points differing from First Embodiment will be primarily described.

In the light receiving optical system, a first light receiving unit 510 is arranged to be conjugate with the center of curvature of the cornea of the eye under examination through an objective lens 310 and a collimator lens 320, in the condition where appropriate operating distance is adjusted by an output from a third light receiving unit 530 being an operating distance optical system and appropriate alignment is adjusted by an output from a second light receiving unit 520 of an alignment optical system.

The front side focus position of a first afocal lens 310 roughly coincides with the cornea of the eye under examination, different from that in First Embodiment.

In addition, a first light receiving optical system 300A is moved and adjusted so that an illumination luminous flux from a first illumination optical system 200A converges toward the center of curvature of the eye 1000 under examination, in the condition where appropriate operating distance and appropriate alignment are adjusted. Whether the illumination luminous flux from the first illumination optical system 200A correctly converges toward the center of curvature of the cornea of the eye 1000 under examination is confirmed by minutely moving the first illumination optical system 200A in the direction of the optical axis and performing movement and adjustment so that the output of the first light receiving unit 510 is maximized before and after the minute movement.

As for the shape of the cornea, first, the first illumination optical system 200A and the first light receiving optical system 300A in conjunction therewith are moved so that the luminous flux from the first illumination optical system 200A converges to the center of curvature of the cornea in the condition where appropriate operating distance is adjusted, and the distance between the position of the apex of the cornea and the converging position of the first light receiving optical system 300A at the time when the output of the first light receiving unit 510 of the first light receiving optical system 300A is maximized corresponds to the radius of curvature of the cornea.

Namely, the adjustment of the appropriate distance is completed.

The specific measuring method and procedures in this Fourth Embodiment are roughly the same as those described in First Embodiment, so that detailed description of the same is omitted.

The Zernike polynomial obtained represents the optical characteristics (shape, radius of curvature, power, etc.) of the cornea.

The other aspects of constitution, action and the like are the same as those in First Embodiment, so that description thereof is omitted.

Fifth Embodiment

Figure 11:
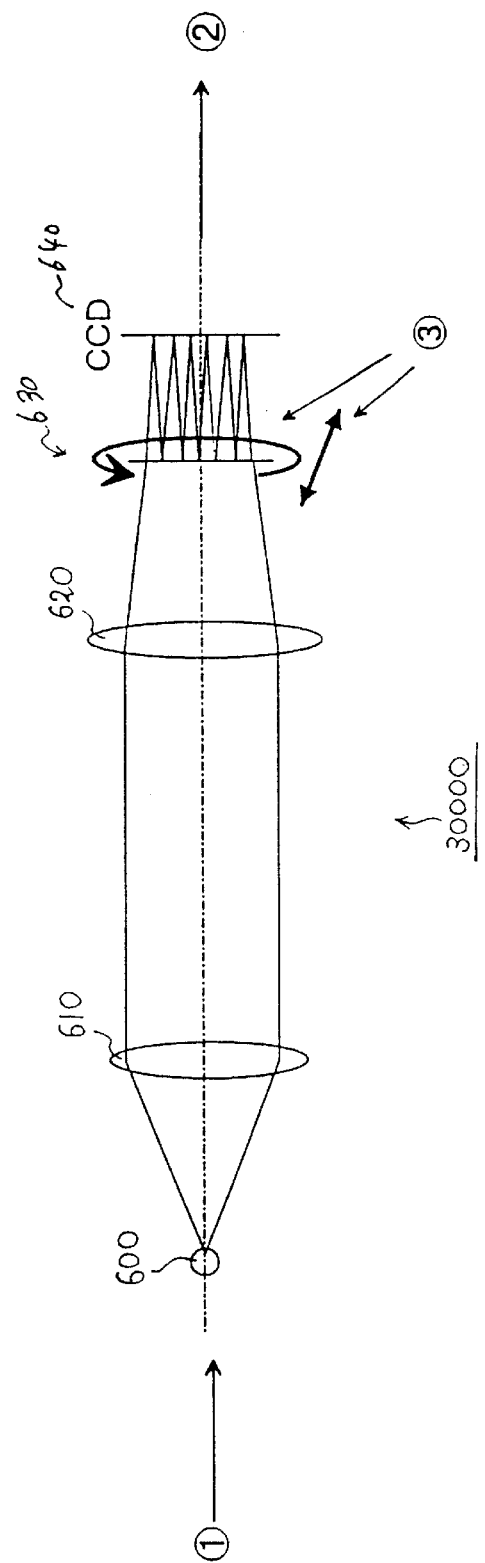
FIG. 11 is a diagram showing the constitution of an optical characteristic measuring apparatus 30000 according to Fifth Embodiment.

An optical characteristic measuring apparatus 30000 according to Fifth Embodiment of the present invention has an optical constitution for measuring the characteristics of an optical lens. As shown in FIG. 11, a luminous flux from a light source 600 is converted into a roughly parallel luminous flux by a collimator lens 610, the luminous flux passes through a lens 620 under measurement, and is led to a first light receiving unit 640 through a first transforming member 630 for transforming the luminous flux converged or diffused by the optical characteristics of the lens 620 into at least nine beams.

The first transforming member 630 is constituted in the same manner as that in First Embodiment so that the first transforming member 630 is rotated or moved while maintaining the positional relationship such that the opening position of the first transforming member 630 interpolates the opening positions.

Figure 12:
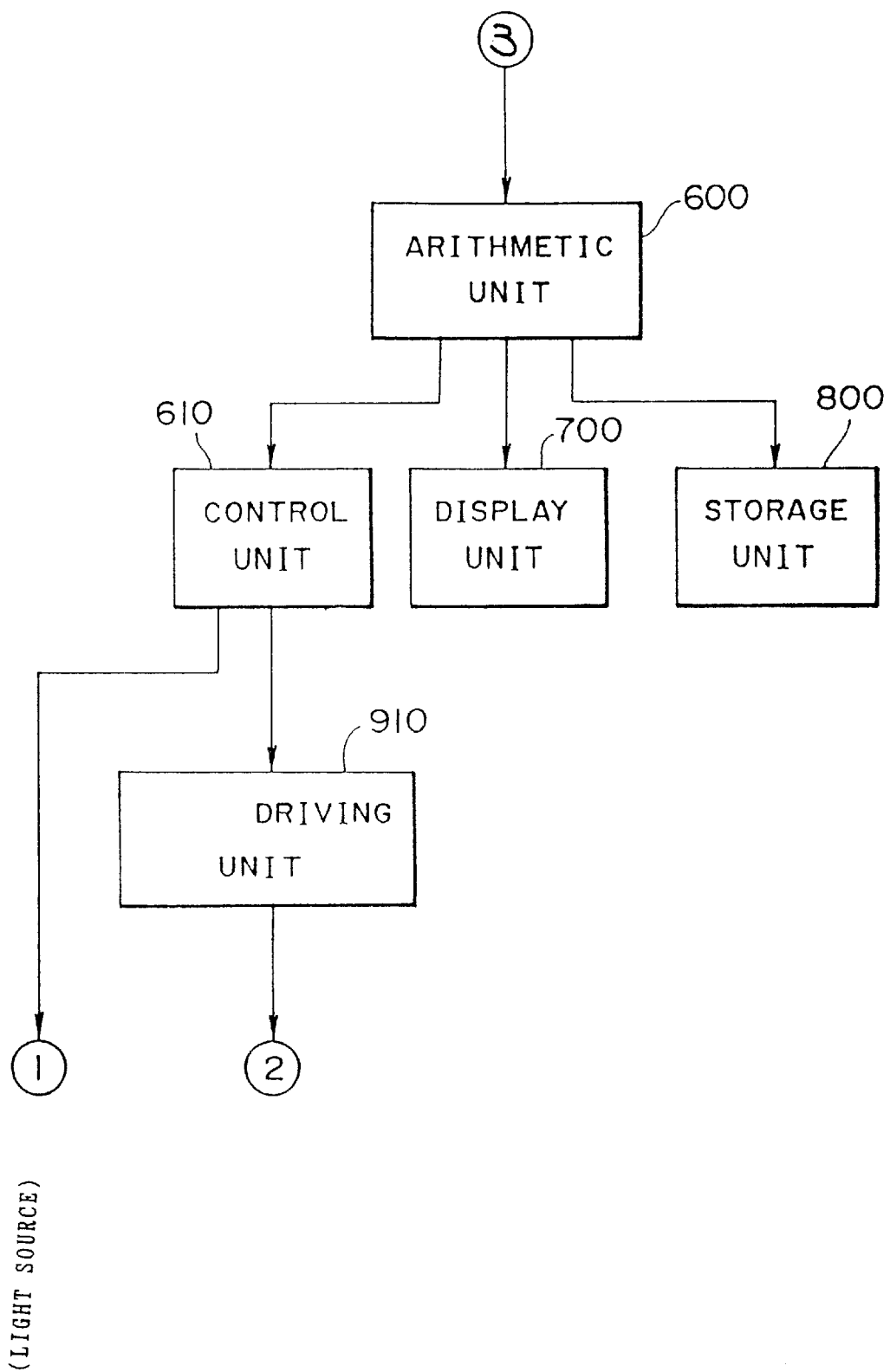
FIG. 12 is a diagram showing the electrical constitution of the optical characteristic measuring apparatus 30000 according to Fifth Embodiment.

As for processing of electrical signals, as shown in FIG. 12, an arithmetic unit 600 receives signals ④, ⑦, ⑩ from a first light receiving unit 510, a second light receiving unit 520 and a third light receiving unit 530, controls the driving of a first light source unit 100 to a fourth light source unit 130 and the driving of a first driving unit 910 to a third driving unit 930, and performs calculation and control of a display unit 700 and a memory 800.

A control unit 610 moves a first illumination optical system 200A in the direction of the optical axis through the first driving unit 910 so that the luminous flux emitted from the first illumination optical system 200A is concentrated roughly toward the center of curvature of the cornea of an eye under measurement through an objective lens, and turns a cylindrical lens so as to correct an astigmatism component of the eye 1000 under measurement.

In addition, the control unit 610 moves the first illumination optical system 200A in the optical axis direction through the second driving unit 910 so that the luminous flux emitted from the first illumination optical system 200A is concentrated roughly toward the center of curvature of the cornea of the eye under measurement through the objective lens, and turns the cylindrical lens so as to correct the astigmatism component of the eye 1000 under measurement.

Figure 13B:
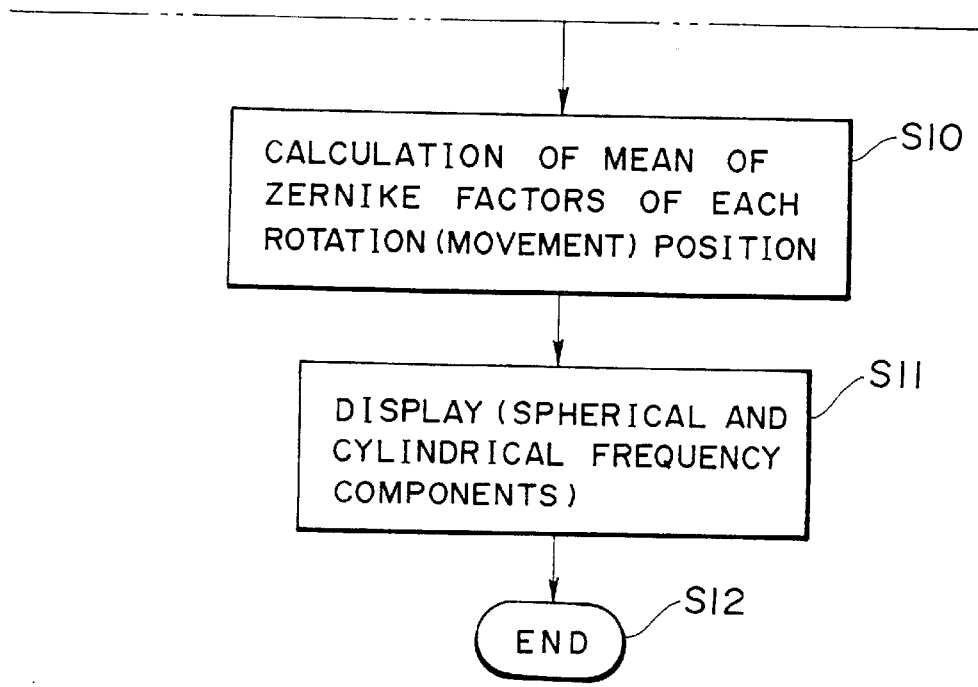
FIG. 13 is a diagram showing the operation of Fifth Embodiment.

Next, a specific measuring method will be described referring to FIG. 13. The operations from S1 to S10 are common with those in FIG. 4, so that the detail thereof is omitted.

In S11, a wave front is constructed based on Zernike factors calculated. Namely, the wave front of the light having passed through the object of measurement is represented by W(X, Y), which is represented with Zernike factors as Expression (3). Besides, main curvatures κ1, κ2 and main direction vectors e(κ₁), e(κ₂) are given by Expression (7).

$$\kappa 1 = \frac{b + \sqrt{b^2 - 4ac}}{2a}, \kappa 2 = \frac{b - \sqrt{b^2 - 4ac}}{2a} \quad \text{Expression (7)}$$

$$e_{kl} = \left(\xi_L, \alpha\xi_1, \xi_1\left(\frac{\partial W}{\partial x} + \alpha\frac{\partial W}{\partial y}\right)\right), e_{k2} \perp e_{pl}$$

$$a = EG - F^2, b = EN + GL - 2FM, c = LN - M^2$$

$$E = 1 + \left(\frac{\partial W}{\partial x}\right)^2, F = \frac{\partial W}{\partial x}\frac{\partial W}{\partial y}, G = 1 + \left(\frac{\partial W}{\partial y}\right)^2$$

$$L = \frac{\frac{\partial^2 W}{\partial x^2}}{\sqrt{1 + \left(\frac{\partial W}{\partial x}\right)^2 + \left(\frac{\partial W}{\partial y}\right)^2}},$$

$$M = \frac{\frac{\partial^2 W}{\partial x \partial y}}{\sqrt{1 + \left(\frac{\partial W}{\partial z}\right)^2 + \left(\frac{\partial W}{\partial y}\right)^2}},$$

$$N = \frac{\frac{\partial^2 W}{\partial y^2}}{\sqrt{1 + \left(\frac{\partial W}{\partial x}\right)^2 + \left(\frac{\partial W}{\partial y}\right)^2}}$$

$$\xi_t = \frac{1}{\sqrt{1 + \alpha^2 + \left(\frac{\partial W}{\partial x} + \alpha'\frac{\partial W}{\partial y}\right)^2}}, \alpha' = \frac{M - \kappa 1 F}{\kappa 1 G - N}$$

Figure 14:
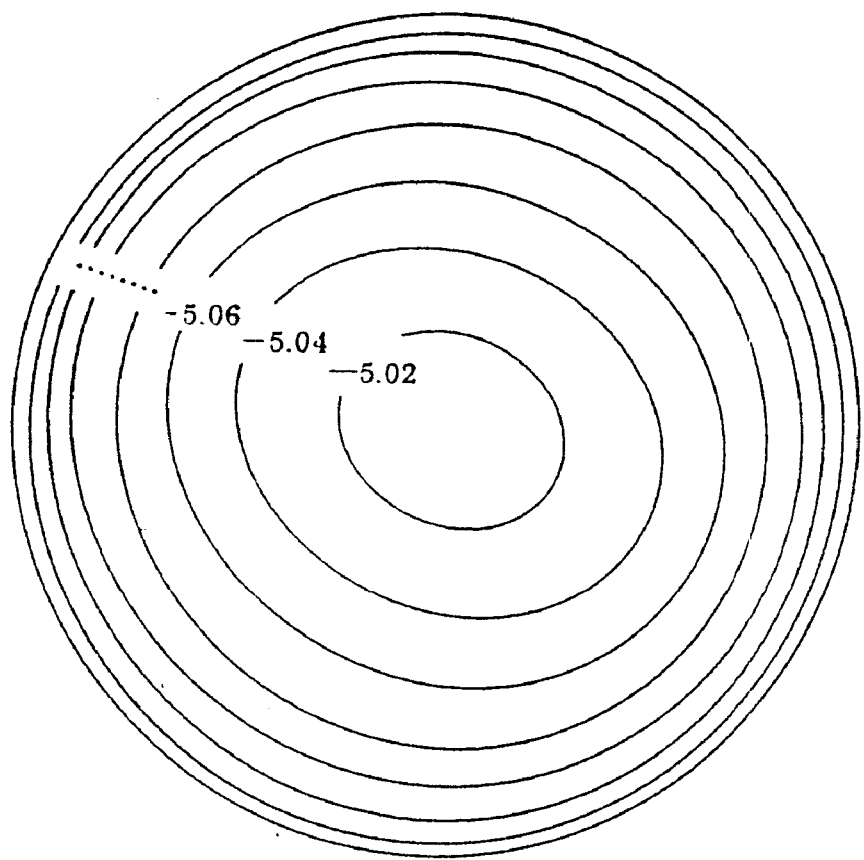
FIG. 14 is a diagram showing a frequency distribution.

The distribution of the main curvature κ1 or κ2 corresponds to the spherical frequency distribution of the lens, and the difference between κ1 and κ2 corresponds to the cylindrical frequency distribution. After the calculations are done, the frequency distribution is displayed graphically as shown in FIG. 14.

Sixth Embodiment

Figure 15:
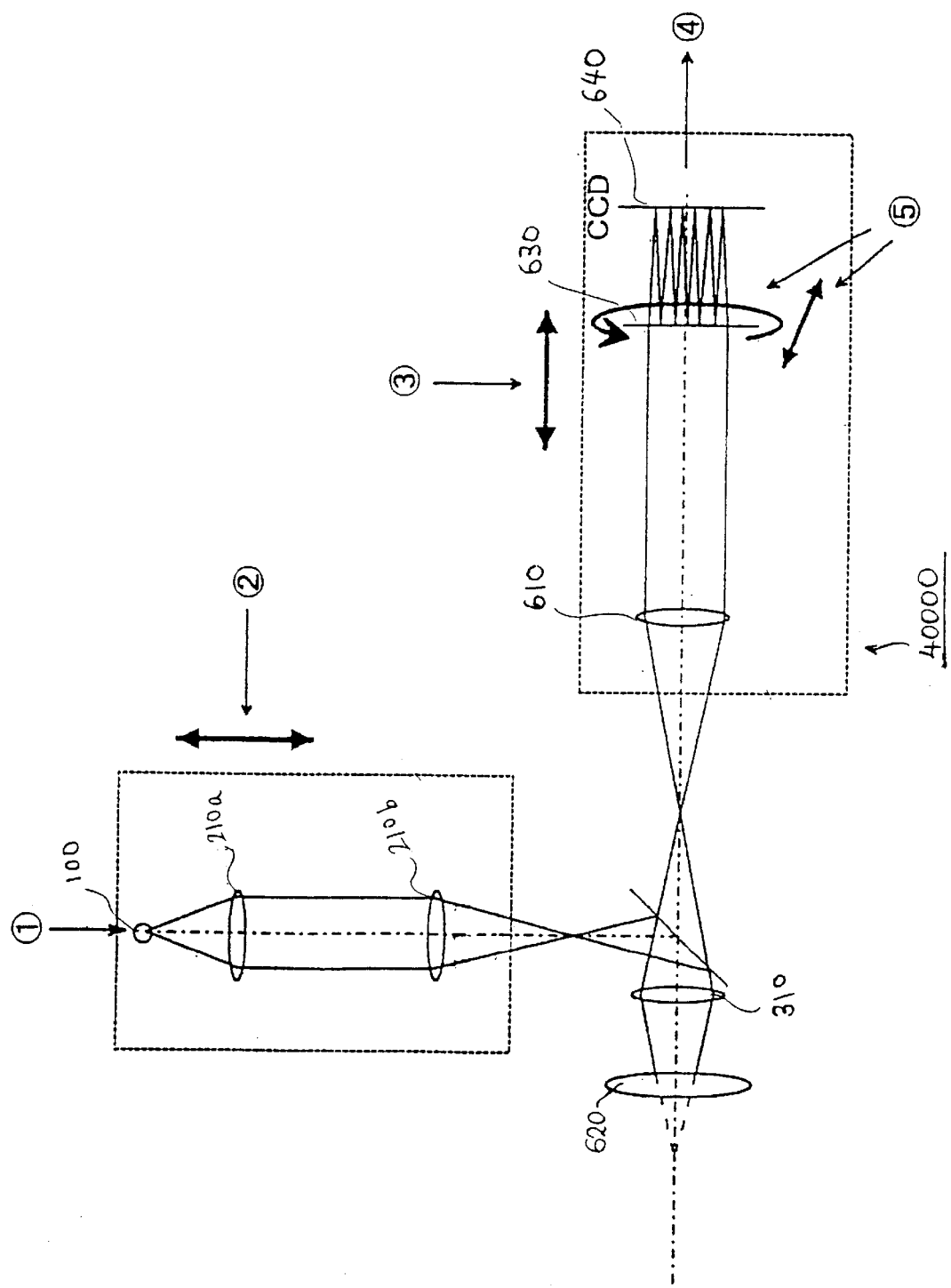
FIG. 15 is a diagram showing the constitution of an optical characteristic measuring apparatus 40000 according to Sixth Embodiment.

An optical characteristic measuring apparatus 40000 according to Fifth Embodiment of the present invention has an optical constitution for the case of measuring characteristics of an optical lens, particularly measuring the shape of the lens surface through the light reflected from the surface. The optical constitution shown in FIG. 15 basically is roughly the same as that shown in FIG. 1 and FIG. 10, so that detailed description thereof is omitted.

A first illumination optical system 200A is for illuminating a minute area on the eyeground of the eye under examination with a luminous flux from a first light source unit 100. The first illumination optical system 200A is for causing a luminous flux to pass through a first collimator lens 210a and a first condensing lens 210b, thereby once converging, and illuminating the converged luminous flux roughly toward the center of curvature of the lens surface under measurement through an objective lens 310. The first illumination optical system 200A is so constructed that the light reflected from the surface of the optical lens 620 under measurement according to the optical characteristics of the lens 620 is condensed by the objective lens 310, is converted into a roughly parallel luminous flux by a collimator lens 610, and is received by a first light receiving unit 640 through a first transforming member 630 for transforming the luminous flux into at least nine beams.

The first transforming member 630 is constituted in the same manner as that in First Embodiment and performs rotation or movement so that the opening position of the first transforming member 630 is moved while maintaining a positional relationship such as to interpolate between opening positions.

Figure 16:
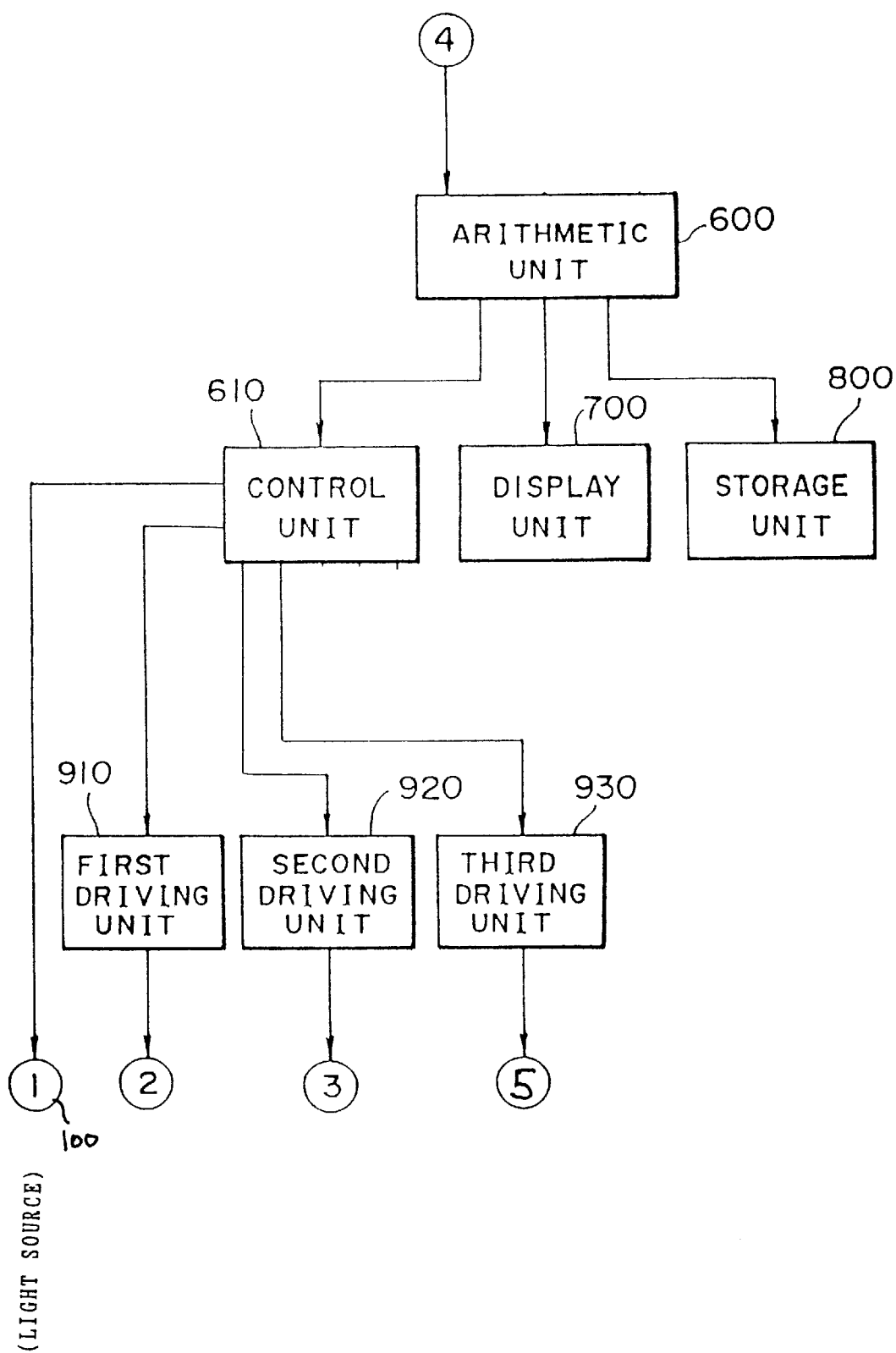
FIG. 16 is a diagram showing the electrical constitution of the optical characteristic measuring apparatus 40000 according to Sixth Embodiment.

As for processing of electrical signals, as shown in FIG. 16, an arithmetic unit receives a signal ④ from a first light receiving unit 600, controls the driving of the first light source unit 100, controls the movements of the first illumination optical system 200A and the first light receiving optical system 300A through a first driving unit 910 to a third driving unit 930, controls the driving of movement and rotation of the transforming member, and controls through calculation a display unit 700 and a memory 800.

The specific measuring method and procedures in Sixth Embodiment are basically the same as those in other embodiments, so that detailed description thereof is omitted.

The principle of operation of the arithmetic unit 600 for determining the optical characteristics of the eye 1000 on the basis of the first signal provided by the first photodetecting device 510 and corresponding to the inclination of light will be explained.

The present invention is intended to measure the wave aberration of the eye.

The coordinate system XY is defined by an x-axis and a Y-axis on the transforming device 400 and a coordinate system xy is defined by an x-axis and a y-axis on the first photodetecting device 510. A wavefront W(X, Y) expressed by Expression (3) is determined by Expressions (1) and (2).

$$\frac{\partial W(X, Y)}{\partial X} = \frac{\Delta x}{f} \quad \text{Expression (1)}$$

$$\frac{\partial W(X, Y)}{\partial Y} = \frac{\Delta y}{f} \quad \text{Expression (2)}$$

$$W(X, Y) = \sum_{i=0}^{n} \sum_{j=0}^{i} c_{ij} Z_{ij}(X, Y) \quad \text{Expression (3)}$$

Both sides of Expression (3) are differentiated by X and Y to obtain derivatives, and the derivatives are substituted into the left sides of Expressions (1) and (2) to obtain a polynomial of $C_{ij}$.

$Z_{ij}$ of Expression (3) is called Zernike polynomial expressed by Expressions (4) and (5).

$$Z_{nm} = R_n^{n-2m}(r) \left\{ \frac{\sin}{\cos} \right\} (n - 2m)\theta \quad \text{Expression (4)}$$

$$R_n^{n-2m}(r) = \sum_{S=0}^{m} (-1)^S \frac{(n-S)!}{S!(m-S)!(n-m-S)!} r^{n-2S} \quad \text{Expression (5)}$$

Unknowns $C_{ij}$ are determined by reducing the mean square error of Expression (6) to a minimum.

$$S(x) = \sum_{i=1}^{\text{data number}} \left[ \left\{ \frac{\partial W(X_i, Y_i)}{\partial X} - \frac{\Delta x_i}{f} \right\}^2 \div \left\{ \frac{\partial W(X_i, Y_i)}{\partial Y} - \frac{\Delta y_i}{f} \right\}^2 \right] \quad \text{Expression (6)}$$

The $C_{ij}$ thus determined are important optical parameters of the eye.

In Zernike polynomial, symbols indicate the followings.

$Z_{10}$, $Z_{11}$: Prisms
$Z_{21}$: S
$Z_{20}$, $Z_{22}$: C, Ax
$Z_{30}$, $Z_{33}$: Arrow aberration
$Z_{31}$, $Z_{32}$: Third-order coma aberration
$Z_{42}$: Third-order spherical aberration
$Z_{41}$, $Z_{43}$: Astigmatism
$Z_{52}$, $Z_{53}$: Fifth-order coma aberration
$Z_{63}$: Fifth-order spherical aberration
$Z_{84}$: Seventh-order spherical aberration Next, rotation and movement of the transforming member 400 will be described in detail.

Movement

Figure 17:
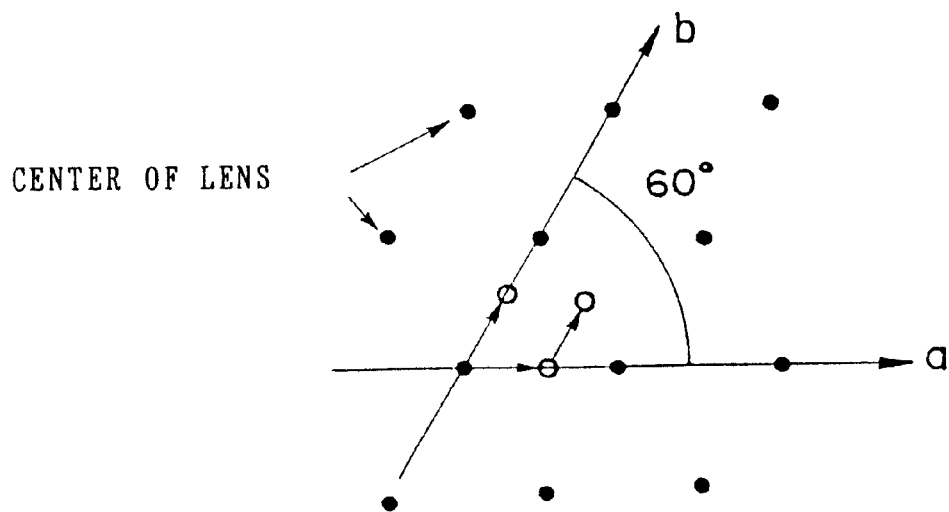
FIG. 17 is a diagram illustrating the movement of a transforming member 400.

First, the movement of the transforming member 400 will be described based on FIG. 17.

Here, in the case of a hexagonal lens, the center of the lens is located on a lattice point of affine coordinates with an including angle of 60 degrees. Normalization is conducted so that the spacing of the lenses on an affine axis becomes 1. It suffices to consider parallel movements in the range of a axis and b axis of:

$$0 < a < 1, \ 0 < b < 1.$$

Where only an appropriate one dimension is considered, when the number of divisions (number of steps) for movement is N, the movement amount is:

$$(\Delta a, \Delta b) = (n/N, m/N)$$

where $0 \leq n < N$ and $0 \leq m < N$.

The number of times of movement is N*N−1. When location of the origin is included, the number of times of movement is N*N, and the number of measurement points is N*N.

Figure 18:
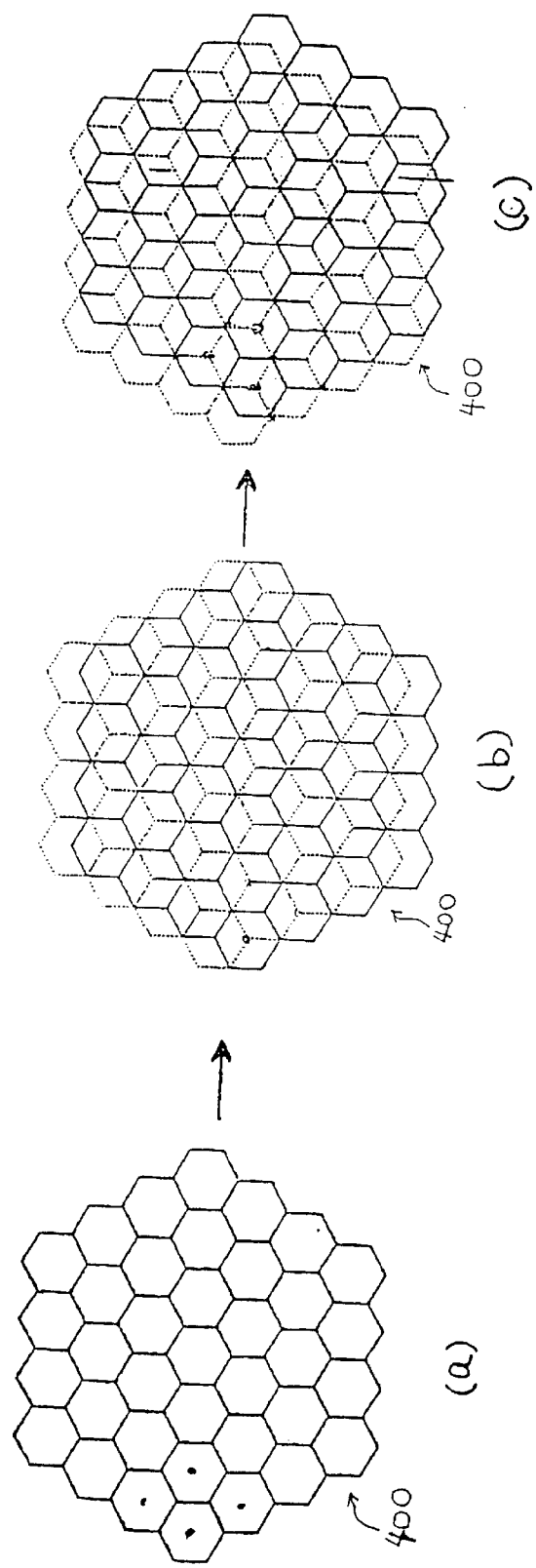
FIG. 18 is a diagram illustrating the movement of the transforming member 400.

As another method of parallel movement, there is also a method in which a movement from FIG. 18(a) to FIG. 18(b) is conducted, and then movement to FIG. 18(c) is conducted.

In the case of a tetragonal lens, the including angle is changed to 90 degrees.

Rotation

Figure 19:
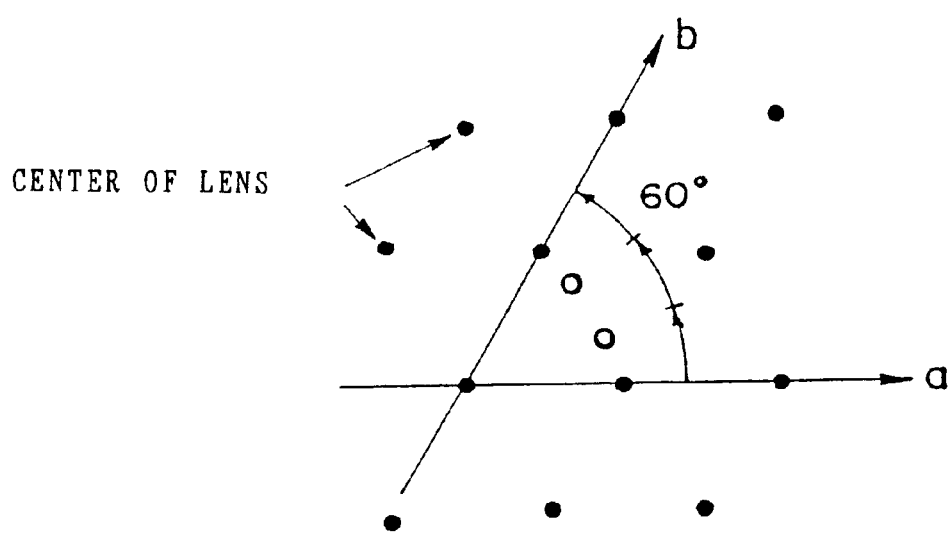
FIG. 19 is a diagram illustrating the rotation of the transforming member 400.

Next, rotation of the transforming member 400 will be described based on FIG. 19.

Here, in the case of a hexagonal lens, the center of the lens is located at a lattice point of affine coordinates with an including angle of 60 degrees. When the center of one lens is rotated, symmetry for every 60 degrees is established.

Therefore, rotation from 0 degree to 60 degrees is equally divided into N pieces, and data is acquired by rotating in N steps.

Figure 20:
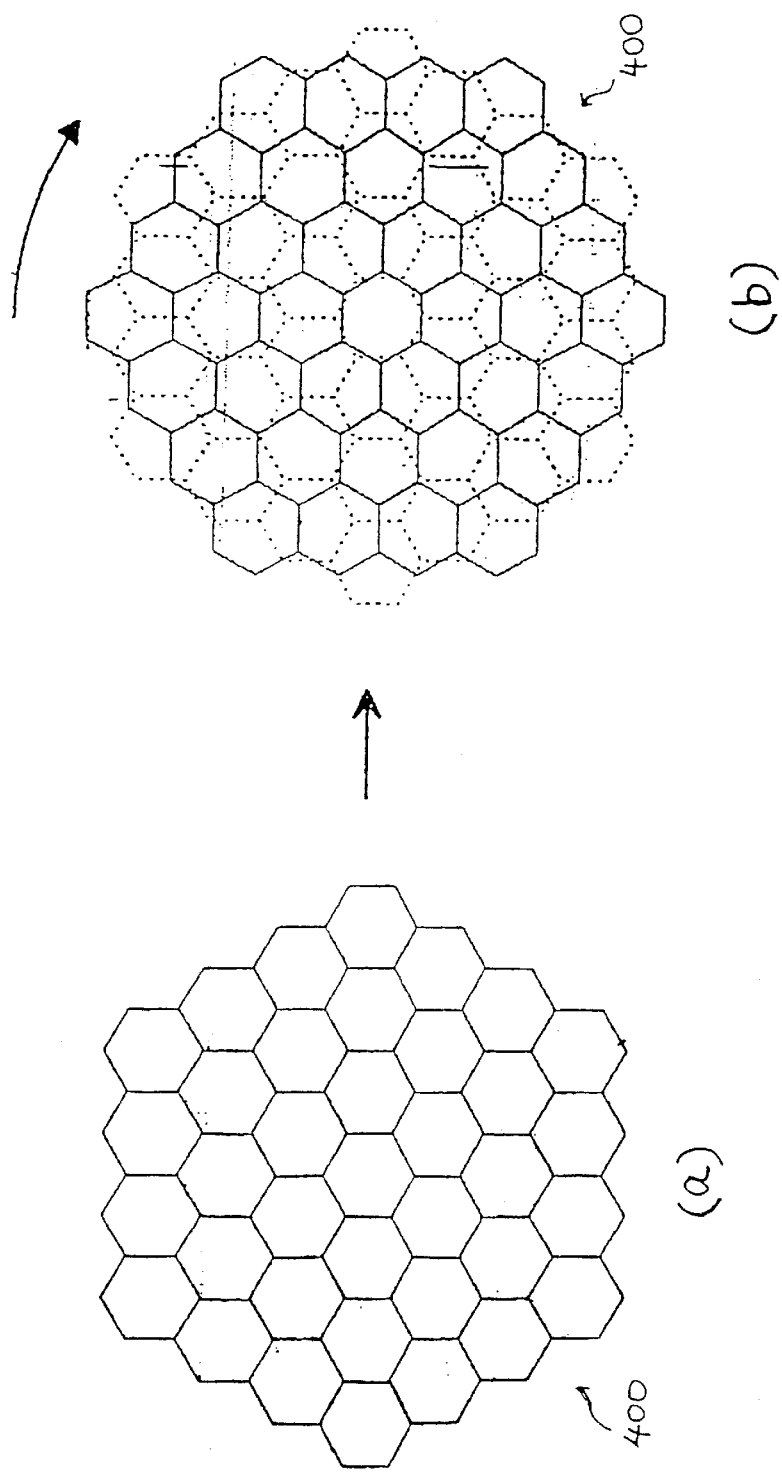
FIG. 20 is a diagram illustrating the rotation of the transforming member 400.

When the transforming member 400 is rotated in the manner described above, for example, rotation from FIG. 20(a) to FIG. 20(b) is attained.

In the case of a tetragonal lens, symmetry for every 90 degrees is established.

In the case of the movement as described above, the opening positions of the transforming member 400 are changed before and after the movement; in the case of the rotation, all the other openings than the opening located at the center of rotation are positionally changed before and after the rotation, and only the opening at the center of rotation remains unchanged positionally.

Seventh Embodiment

Figure 21:
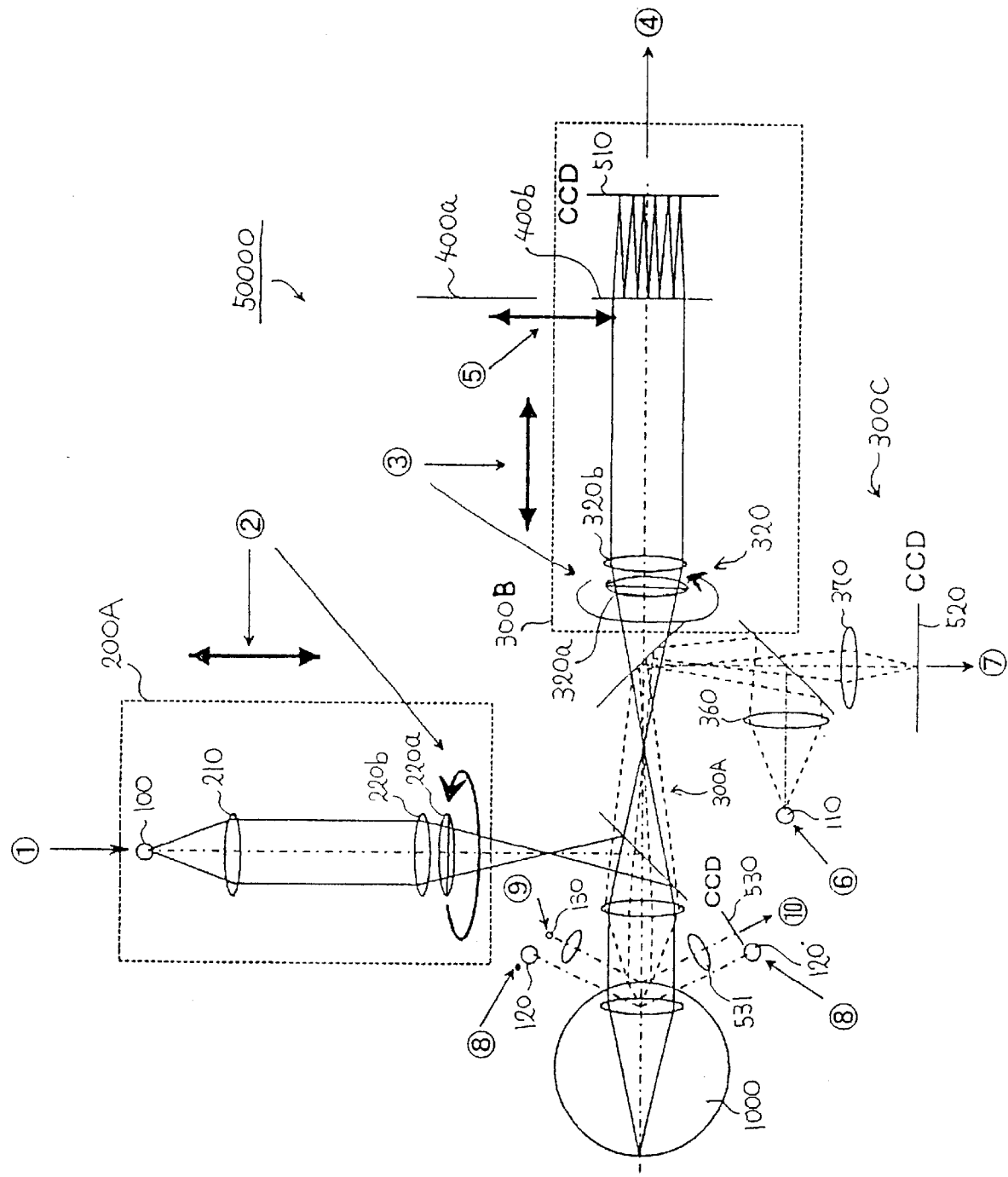
FIG. 21 is a diagram showing the constitution of an optical characteristic measuring apparatus 50000 according to Seventh Embodiment.

An optical characteristic measuring apparatus 50000 according to Seventh Embodiment of the present invention is, as shown in FIG. 21, provided with at least two kinds of first transforming members 400, changeover from one first transforming member 400a to the other first transforming member 400b is conducted by a linear movement or a rotational movement, and the first transforming member 400a changed over is inserted into an optical path.

To provide two kinds of first transforming members 400 means not only the case where opening positions are disposed at different spacings but also the case where the opening positions are at the same spacing but the directions of the openings are different.

By this, for example, the same transforming members are so disposed that the angle with the center as a reference is changed before and after the changeover, whereby the same action as that in the case of rotating the first transforming member 400 can be obtained.

As a component corresponding to the second collimator lens 320 in First Embodiment of FIG. 1, a second cylindrical lens 320a and a second relay lens 320b are provided in this Seventh Embodiment.

The second cylindrical lens 320a is rotated by a second driving unit 920.

Figure 22:
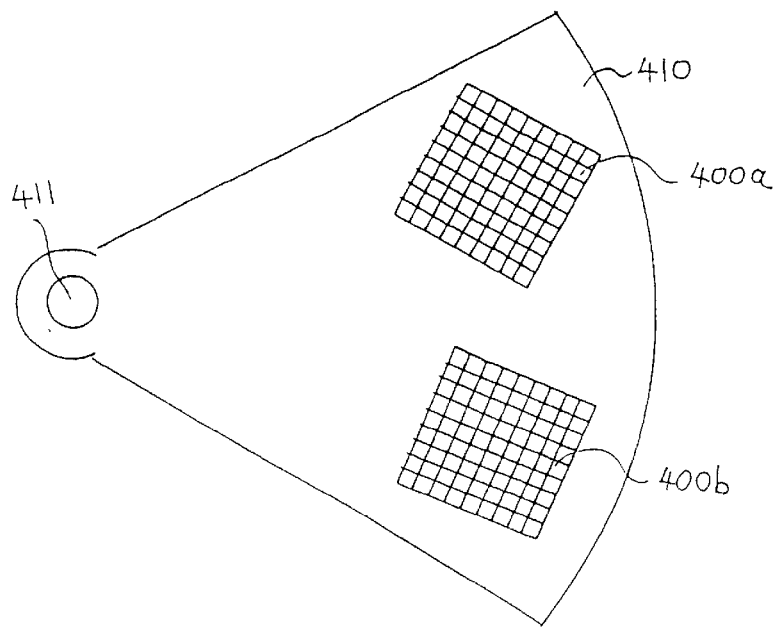
FIG. 22 is a diagram showing an embodiment of rotational movement of a substrate 410.

FIG. 22 shows a system in which changeover from one first transforming member 400a to the other first transforming member 400b is conducted by a rotational movement. A substrate 410 is provided with a rotation center portion 411, the first transforming member 400a and the first transforming member 400b, and the substrate 410 can be rotated with the rotation center portion 411 as a center.

The substrate 410 is controlledly rotated by a third driving unit 930. The third driving unit 930 may be constituted of any mechanism that can rotate the substrate 410 with the rotation center portion 411 as a center.

Figure 23:
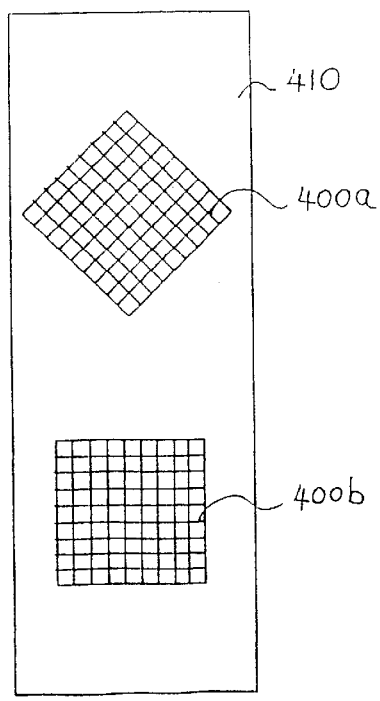
FIG. 23 is a diagram showing an embodiment of linear movement of the substrate 410.

FIG. 23 shows a system in which changeover from one first transforming member 400a to the other first transforming member 400b is conducted by a linear movement. A substrate 410 is provided with the first transforming member 400a and the first transforming member 400b, and can be moved in a linear direction.

The substrate 410 is controlledly linearly moved by the third driving unit 930. The third driving unit 930 may be constituted of any mechanism that can linearly move the substrate 410.

The other aspects of constitution, action and the like are the same as those in other embodiment, so that description thereof is omitted.

While the illumination luminous flux to the eyeground is incident in a broad form (so-called double pulse) as shown in the drawings in the present description, it goes without saying that the luminous flux may be a thin beam (so-called single pulse).

In the above description, the first transforming member 400 can transform the luminous flux into at least nine beams, whereby the opening positions of the first transforming member 400 are moved to at least 17 points by movement or rotation, and measurement data can be obtained at those points; by the data obtained from the openings at the at least 17 points, it is possible to measure high-order aberration components other than the spherical component and astigmatism components.

The present invention constituted as above comprises a first light source for emitting a luminous flux of a first wavelength, a first illumination optical system for illuminating a minute area on the retina of an eye under examination with the luminous flux from the first light source, a first light receiving optical system for leading a portion of the luminous flux reflected back from the retina of the eye to a first light receiving unit through a first transforming member for transforming the reflected luminous flux into at least nine beams, a position change unit for changing the positions of the beams transformed by the first transforming member, and an arithmetic unit for determining optical characteristics of the dye under examination based on a first signal from the first light receiving unit corresponding to the angle of inclination of the luminous flux. Therefore, by using a transforming member for transforming into a small number of beams and moving the transforming member so as to obtain measurement results at a larger number of points, it is possible to measure with higher precision than that expected from the number of beams generated by the transforming member.

Besides, the density of the openings for transforming into a plurality of beams can be made coarse, so that the diameter of the openings can be larger, and light reception signals with higher intensity can be obtained effectively.

Industrial Applicability

The present invention relates to an apparatus for precise measurement of optical characteristics, and particularly, has an object to provide an optical characteristic measuring apparatus comprising a position change unit for changing the positions of beams transformed by a first transforming member, whereby optical characteristics of an object of measurement can be determined.

What is claimed is:

1. An optical characteristic measuring apparatus comprising:

a first light source for emitting a luminous flux of a first wavelength;

a first illumination optical system for illuminating a minute area on the retina of an eye under examination with said luminous flux from said first light source;

a light receiving optical system for leading light to a first light receiving unit through a first transforming member for transforming the luminous flux having undergone at least one of transmission and reflection at at least one surface of the object of measurement into at least nine beams;

a position change unit for changing the positions of said beams transformed by said first transforming member; and an arithmetic unit for determining optical characteristics of said object of measurement based on a first signal from said first light receiving unit, said first signal corresponding to the angle of inclination of the luminous flux.

2. An optical characteristic measuring apparatus as set forth in claim 1, wherein said position change unit changes the positions of said beams transformed by said first transforming member by at least one of linear movement and rotational movement of said first transforming member.

3. An optical characteristic measuring apparatus as set forth in claim 2, wherein said position change unit moves said first transforming member to at least one of mechanical constitution and optical constitution.

4. An optical characteristic measuring apparatus as set forth in claim 1, wherein said position change unit changes the positions of said beams transformed by said first transforming member by at least one of linear movement and rotational movement of said first transforming member, whereby the transformed beam positions after said change are located at substantially middle positions of the transformed beams before said change.

5. An optical characteristic measuring apparatus as set forth in claim 1, wherein said arithmetic unit calculates optical characteristics of said object of measurement based on data before and after said change of beam positions, and determines a process according to deviations of the optical characteristics.

6. An optical characteristic measuring apparatus as set forth in claim 5, wherein said arithmetic unit prompts re-measurement based on the data before and after said change of beam positions when said optical characteristics of said object of measurement calculated respectively based on the data before and after said change are discrepant from each other by not less than a predetermined value.

7. An optical characteristic measuring apparatus as set forth in claim 5, wherein said arithmetic unit determines measurement results through mean values of optical characteristics based on the data before and after said change of beam positions when the optical characteristics of said object of measurement calculated respectively based on the data before and after said change are within predetermined values.

8. An optical characteristic measuring apparatus as set forth in claim 5, wherein said arithmetic unit determines measurement results based on data obtained by synthesizing the data before and after said change, based on the data before and after said change of beam positions, when the optical characteristics of said object of measurement calculated respectively based on the data before and after said change are within predetermined values.

9. An optical characteristic measuring apparatus as set forth in claim 1, wherein said object of measurement is an eye under examination, said at least one surface of said object of measurement is the cornea surface, said first illumination optical system illuminates the cornea, said first light receiving optical system receives light through said first transforming member for transforming the luminous flux reflected by said cornea surface into at lest nine beams, and said arithmetic unit determines the shape of the cornea of the eye under examination as optical characteristic of said object.

10. An optical characteristic measuring apparatus as set forth in claim 1, wherein said object of measurement is an eye under examination, said at least one surface of said object of measurement is the retina, said first illumination optical system illuminates said retina, said first light receiving optical system receives light through said first transforming member for transforming the luminous flux reflected by said retina into at least nine beams, and said arithmetic unit determines the refracting power of said eye under examination as optical characteristic of said object.

11. An optical characteristic measuring apparatus as set forth in claim 1, wherein said object of measurement is an optical lens, said first illumination optical system illuminates an illumination luminous flux such as to transmit through or be reflected by said optical lens, and said first light receiving optical system receives light through said first transforming member for transforming said illumination luminous flux having transmitted through or been reflected by said optical lens into at least nine beams.

12. A optical characteristic measuring apparatus as set forth in claim 1, wherein at least two kinds of said first transforming member are provided, a changeover from one of the said first transforming members to the other of said first transforming members is carried out by linear movement or rotational movement, and said first transforming member thus changed over is inserted into an optical path.

* * * * *